United States Patent
John Archibald

(10) Patent No.: US 12,336,787 B2
(45) Date of Patent: Jun. 24, 2025

(54) DIFFERENTIAL BLOOD PRESSURE ESTIMATION BASED ON TWO-DIMENSIONAL PLETHYSMOGRAPHY IMAGES

(71) Applicant: QUALCOMM Incorporated, San Diego, CA (US)

(72) Inventor: Fitzgerald John Archibald, Richmond Hill (CA)

(73) Assignee: QUALCOMM Incorporated, San Diego, CA (US)

( * ) Notice: Subject to any disclaimer, the term of this patent is extended or adjusted under 35 U.S.C. 154(b) by 127 days.

(21) Appl. No.: 18/179,873

(22) Filed: Mar. 7, 2023

(65) Prior Publication Data

US 2024/0298902 A1    Sep. 12, 2024

(51) Int. Cl.
*A61B 5/00* (2006.01)

(52) U.S. Cl.
CPC ............ *A61B 5/0095* (2013.01); *A61B 5/743* (2013.01)

(58) Field of Classification Search
CPC .............................. A61B 5/0095; A61B 5/743
See application file for complete search history.

(56) References Cited

U.S. PATENT DOCUMENTS

| | | | |
|---|---|---|---|
| 2013/0109947 A1* | 5/2013 | Wood ...................... | A61B 5/021 600/407 |
| 2022/0175258 A1 | 6/2022 | Kitchens et al. | |

FOREIGN PATENT DOCUMENTS

WO    WO-2021114134 A1    6/2021

OTHER PUBLICATIONS

Garcia-Uribe A., et al., "Noninvasive Measurement of Internal Jugular Venous Oxygen Saturation by Photoacoustic Imaging", Progress in Biomedical Optics and Imaging, SPIE—International Society for Optical Engineering, Bellingham, WA, US, vol. 8943, Mar. 3, 2014, pp. 89431M-1-89431M-6, XP060029591, pp. 2, 3, figures 1-3.
International Search Report and Written Opinion—PCT/US2024/011502—ISA/EPO—Apr. 29, 2024.

\* cited by examiner

*Primary Examiner* — Michael T Rozanski
(74) *Attorney, Agent, or Firm* — QUALCOMM Incorporated

(57) ABSTRACT

Some disclosed methods involve controlling, via a control system, a light source system to emit a plurality of light pulses into biological tissue, the biological tissue including blood and blood vessels at depths within the biological tissue. Such methods may involve receiving, by the control system, signals from the piezoelectric receiver corresponding to acoustic waves emitted from portions of the biological tissue, the acoustic waves corresponding to photoacoustic emissions from the blood and the blood vessels caused by the plurality of light pulses. Such methods may involve generating, by the control system, a plethysmography image based on heart rate waveforms in the signals, and determining a blood pressure differential by comparing the plethysmography image with a reference plethysmography image.

30 Claims, 13 Drawing Sheets

DIFFERENTIAL BLOOD PRESSURE ESTIMATION BASED ON TWO-DIMENSIONAL PLETHYSMOGRAPHY IMAGES

TECHNICAL FIELD

This disclosure relates generally to non-invasive blood pressure estimation and blood vessel monitoring.

DESCRIPTION OF RELATED TECHNOLOGY

A variety of different sensing technologies and algorithms are being investigated for use in various biomedical applications, including health and wellness monitoring. This push is partly a result of the limitations in the usability of traditional measuring devices for continuous, noninvasive and ambulatory monitoring. For example, a sphygmomanometer is an example of a traditional blood pressure monitoring device that utilizes an inflatable cuff to apply a counter pressure to a region of interest (for example, around an upper arm of a subject). The pressure exerted by the inflatable cuff is designed to restrict arterial flow in order to provide a measurement of systolic and diastolic pressure. Such traditional sphygmomanometers inherently affect the physiological state of the subject, which can introduce an error in the blood pressure measurements. Such sphygmomanometers also can affect the psychological state of the subject, which can manifest itself in a physiological state change, and thus, introduce an error in the blood pressure measurements. For example, such devices are often used primarily on isolated occasions, for example, when a subject visits a doctor's office or is being treated in a hospital setting. Naturally, some subjects experience anxiety during such occasions, and this anxiety can influence (for example, increase) the user's blood pressure as well as heart rate.

For these and other reasons, such devices may not provide an accurate estimation or "picture" of blood pressure, and a user's health in general, over time. While implanted or otherwise invasive devices may provide better estimates of blood pressure over time, such invasive devices generally involve greater risk than noninvasive devices and are generally not suitable for ambulatory use.

SUMMARY

The systems, methods and devices of this disclosure each have several aspects, no single one of which is solely responsible for the desirable attributes disclosed herein.

One innovative aspect of the subject matter described in this disclosure can be implemented in an apparatus, or in a system that includes the apparatus. The apparatus may include an ultrasonic receiver (e.g., a piezoelectric receiver), a light source system and a control system. The control system may include one or more general purpose single-or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

The control system may be configured for controlling the light source system to emit a plurality of light pulses into biological tissue. The biological tissue may, for example, include blood and blood vessels at depths within the biological tissue. The control system may be configured for receiving signals from the piezoelectric receiver corresponding to acoustic waves emitted from portions of the biological tissue. The acoustic waves may, for example, correspond to photoacoustic emissions from the blood and the blood vessels caused by the plurality of light pulses. The control system may be configured for generating a plethysmography image based on heart rate waveforms in the signals, and determining a blood pressure differential by comparing the plethysmography image with a reference plethysmography image.

According to some implementations, the control system may be further configured for displaying the blood pressure differential on a display. According to some implementations, the reference plethysmography image may correspond to a first heart rate cycle and the plethysmography image corresponds to a second heart rate cycle. According to some implementations, the control system may be further configured for time-normalizing the plethysmography image and the reference plethysmography image. According to some implementations, the plethysmography image may comprise a depth time dimension and a pulse time dimension.

According to some implementations, the control system may be further configured for identifying a ground truth blood pressure and determining an absolute blood pressure based on the ground truth blood pressure and the blood pressure differential. According to some implementations, the control system may be further configured for displaying the absolute blood pressure on a display. According to some implementations, the ground truth blood pressure may comprise a cuff-based blood pressure.

According to some implementations, the control system may be further configured for generating the reference plethysmography image based on a first raw plethysmography signal and generating the plethysmography image based on a second raw plethysmography signal. According to some implementations, the light source system may be configured for emitting a plurality of light pulses at a pulse repetition frequency between 10 Hz and 1 MHz.

Other innovative aspects of the subject matter described in this disclosure can be implemented in a method, such as a biometric method. The method may involve controlling, via a control system, a light source system to emit a plurality of light pulses into biological tissue. The biological tissue may, for example, include blood and blood vessels at depths within the biological tissue. The method may involve receiving, by the control system, signals from a piezoelectric receiver, the signals corresponding to acoustic waves emitted from portions of the biological tissue. The acoustic waves may, for example, correspond to photoacoustic emissions from the blood and the blood vessels caused by the plurality of light pulses. The method may involve generating, by the control system, a plethysmography image based on heart rate waveforms in the signals. The method may involve determining, by the control system, a blood pressure differential by comparing the plethysmography image with a reference plethysmography image.

According to some implementations, the method may further involve displaying the blood pressure differential on a display. According to some implementations, the reference plethysmography image may correspond to a first heart rate cycle and the plethysmography image corresponds to a second heart rate cycle. According to some implementations, the method may further involve time-normalizing the plethysmography image and the reference plethysmography image. According to some implementations, the plethysmography image may comprise a depth time dimension and a pulse time dimension.

According to some implementations, the method may further involve identifying a ground truth blood pressure and determining an absolute blood pressure based on the ground truth blood pressure and the blood pressure differential. According to some implementations, the method may further involve displaying the absolute blood pressure on a display. According to some implementations, the ground truth blood pressure may comprise a cuff-based blood pressure.

According to some implementations, the method may further involve generating the reference plethysmography image based on a first raw plethysmography signal and generating the plethysmography image based on a second raw plethysmography signal. According to some implementations, the light source system may be configured for emitting a plurality of light pulses at a pulse repetition frequency between 10 Hz and 1 MHz.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

One such method may controlling, via a control system, a light source system to emit a plurality of light pulses into biological tissue. The biological tissue may, for example, include blood and blood vessels at depths within the biological tissue. The method may involve receiving, by the control system, signals from a piezoelectric receiver, the signals corresponding to acoustic waves emitted from portions of the biological tissue. The acoustic waves may, for example, correspond to photoacoustic emissions from the blood and the blood vessels caused by the plurality of light pulses. The method may involve generating, by the control system, a plethysmography image based on heart rate waveforms in the signals. The method may involve determining, by the control system, a blood pressure differential by comparing the plethysmography image with a reference plethysmography image.

According to some implementations, the method may further involve displaying the blood pressure differential on a display. According to some implementations, the reference plethysmography image may correspond to a first heart rate cycle and the plethysmography image corresponds to a second heart rate cycle. According to some implementations, the method may further involve time-normalizing the plethysmography image and the reference plethysmography image. According to some implementations, the plethysmography image may comprise a depth time dimension and a pulse time dimension.

According to some implementations, the method may further involve identifying a ground truth blood pressure and determining an absolute blood pressure based on the ground truth blood pressure and the blood pressure differential. According to some implementations, the method may further involve displaying the absolute blood pressure on a display. According to some implementations, the ground truth blood pressure may comprise a cuff-based blood pressure.

According to some implementations, the method may further involve generating the reference plethysmography image based on a first raw plethysmography signal and generating the plethysmography image based on a second raw plethysmography signal. According to some implementations, the light source system may be configured for emitting a plurality of light pulses at a pulse repetition frequency between 10 Hz and 1 MHz.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1A:
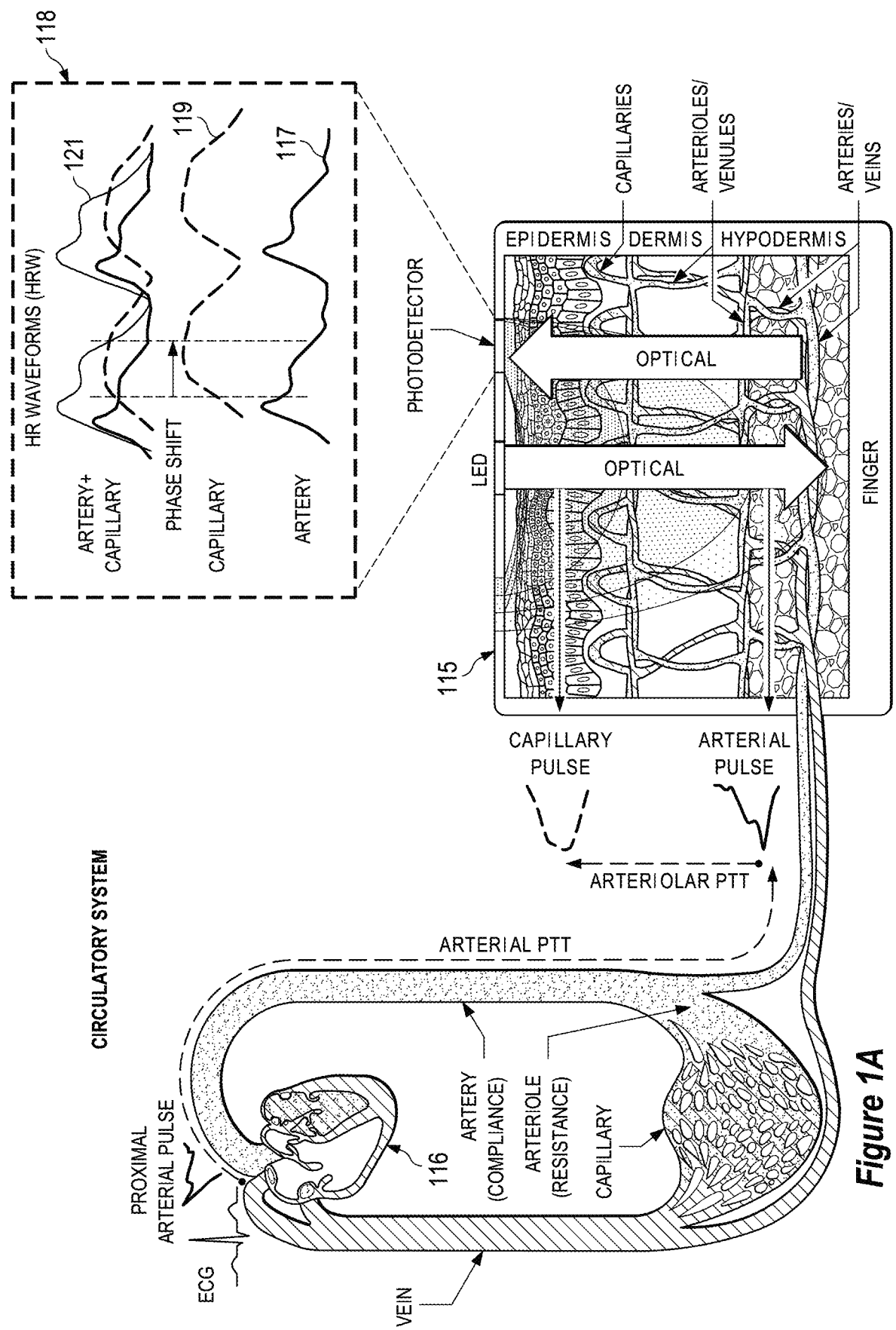
FIG. 1A shows an example of a blood pressure monitoring device based on photoplethysmography (PPG).

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Also of note, the conjunction "or" as used herein is intended in the inclusive sense where appropriate unless otherwise indicated; that is, the phrase "A, B or C" is intended to include the possibilities of A individually; B individually; C individually; A and B and not C; B and C and not A; A and C and not B; and A and B and C. Similarly, a phrase referring to "at least one of" a list of items refers to any combination of those items, including single members. As an example, the phrase "at least one of A, B, or C" is intended to cover the possibilities of at least one of A; at least one of B; at least one of C; at least one of A and at least one of B; at least one of B and at least one of C; at least one of A and at least one of C; and at least one of A, at least one of B and at least one of C.

Various aspects relate generally to blood pressure monitoring, and more particularly to non-invasive blood pressure monitoring using plethysmography. Some aspects more specifically relate to differential blood pressure estimation based on two-dimensional (2D) plethysmography images. In some examples, photoacoustic plethysmography (PAPG) can be conducted to obtain raw 2D PAPG data. In some examples, the raw 2D PAPG data can be processed to extract and normalize plethysmography images corresponding to heart rate cycles. In some examples, a blood pressure differential associated with a given heart rate cycle can be determined by comparing a plethysmography image corresponding to that heart rate cycle with a plethysmography image corresponding to a reference heart rate cycle. In some examples, an absolute blood pressure can be determined based on the differential blood pressure and a ground truth blood pressure associated with the reference heart rate cycle.

In some examples, the comparison of the plethysmography images can be conducted using a raw 2D data deep learning network (DLN) that accepts the plethysmography images as inputs. In some examples, the raw 2D data DLN can generate a differential blood pressure estimate based on the plethysmography images. In some examples, outputs of the DLN can be passed as inputs to a fusion neural network (NN). In some examples, the fusion NN can also accept, as inputs, the outputs of a one-dimensional (1D) heart rate waveform (HRW) DLN. In some examples, heart rate waveforms can be extracted from the raw 2D PAPG data and segmented by heart rate cycle, and the 1D HRW DLN can generate a second differential blood pressure estimate based on heart rate waveform segments corresponding to the given heart rate cycle and the reference heart rate cycle. In some examples, the fusion NN can determine the blood pressure differential based on the outputs of the raw 2D data DLN and the 1D HRW DLN.

Particular implementations of the subject matter described in this disclosure can be implemented to realize one or more of the following potential advantages. According to some implementations, the use of a deep learning network to estimate differential blood pressure based on plethysmography images obtained from raw 2D PAPG data can yield more accurate differential blood pressure estimates. In some implementations, more accurate blood pressure estimates can be obtained by conducting blood pressure estimation using a fusion neural network that accepts, as inputs, both predictive factors generated, via PAPG image construction and segmentation, by a raw 2D data deep learning network and predictive factors generated, via heart rate wave generation and segmentation, by a second deep learning network. In some implementations, the accuracy of blood pressure estimation can be further increased by using differential blood pressure predictions to calibrate blood pressure estimation.

Some implementations of the portable monitoring devices described herein also are designed to consume relatively little power, enabling continuous wearing and monitoring of a biological signal of interest, such as blood pressure, over extended durations of time (for example, hours, days, weeks or even a month or more) without external calibration, recharging or other interruption. Continuous monitoring provides greater prognostic and diagnostic value than isolated measurements, for example, obtained in a hospital or doctor's office setting. Some implementations of the portable or "ambulatory" monitoring devices described herein also are designed with small form factors and with housings that can be coupled to a subject (also referred to herein as a "patient," "person" or "user") so as to be wearable, noninvasive, and nonrestrictive of ambulatory use. In other words, some implementations of the ambulatory monitoring devices described herein do not restrict the free uninhibited motion of a subject's arms or legs enabling continuous or periodic monitoring of cardiovascular characteristics such as blood pressure even as the subject is mobile or otherwise engaged in a physical activity. Not only do such devices not interfere with the subject's daily or other desired activities, they also may encourage continuous wearing by virtue of such non-interference. In some implementations, it can further be desirable that the subject may have no notion about when the sensing device(s) of the ambulatory monitoring device is actually performing measurements.

Moreover, some disclosed implementations provide advantages compared to previously-deployed non-invasive blood pressure monitoring devices, such as those based on photoplethysmography (PPG). PPG-based blood pressure monitoring devices are not optimal because PPG superimposes data corresponding to the blood volume of all illuminated blood vessels (arteries, veins, etc.), each of which exhibit unique blood volume changes over time, thereby producing a blended signal that is not closely correlated to blood pressure and is susceptible to drift. In contrast, some disclosed devices apply depth-discriminated photoacoustic plethysmography (PAPG) methods, which can distinguish artery heart rate waveforms from vein heart rate waveforms and other heart rate waveforms. Blood pressure estimation based on depth-discriminated PAPG methods can be substantially more accurate than blood pressure estimation based on PPG-based methods.

Continuous blood pressure monitoring can be important component of patient care with respect to a wide variety of medical conditions. According to some approaches, continuous blood pressure monitoring can be established using an implanted, or otherwise invasive device, such as a catheter. However, an invasive blood pressure monitoring device can negatively impact patient comfort, can create a risk of infection, and can be unsuitable for ambulatory use. In many cases, it may be desirable to conduct continuous, non-invasive and ambulatory monitoring of a patient's blood pressure monitoring.

Some non-invasive blood pressure monitoring devices can monitor blood pressure using plethysmography. In the general sense, plethysmography involves measuring changes in the volume of an organ, a part of the body, or the body as a whole. Blood pressure monitoring using plethysmography generally involves estimating blood pressure based on measurements of volumetric changes in the blood in a part of the body.

Photo plethysmography (PPG) is one type of plethysmography that can be used for blood pressure monitoring. PPG involves transmitting light onto an area of human tissue, such as tissue of a finger, measuring light reflected from the tissue, and analyzing the reflected light measurements to detect volumetric changes in the blood of the illuminated area.

FIG. 1A shows an example of a blood pressure monitoring device based on PPG. FIG. 1A shows examples of arteries, veins, arterioles, venules and capillaries of a circulatory system, including those inside a finger 115. In the example shown in FIG. 1A, an electrocardiogram sensor has detected a proximal arterial pulse near the heart 116.

According to the example shown in FIG. 1A, a light source that includes one or more light-emitting diodes (LEDs) has transmitted light (in some examples, green, red, and/or near-infrared (NIR) light) that has penetrated the tissues of the finger 115 in an illuminated zone. Reflections from these tissues, detected by the photodetector, may be used to detect volumetric changes in the blood of the illuminated zone of the finger 115 that correspond to heart rate waveforms.

As shown in the heart rate waveform graphs 118 of FIG. 1A, the capillary heart rate waveform 119 is differently-shaped and phase-shifted relative to the artery heart rate waveform 117. In this simple example, the detected heart rate waveform 121 is a combination of the capillary heart rate waveform 119 and the artery heart rate waveform 117. In some instances, the responses of one or more other blood vessels may also be part of the heart rate waveform 121 detected by a PPG-based blood pressure monitoring device.

Figure 1B:
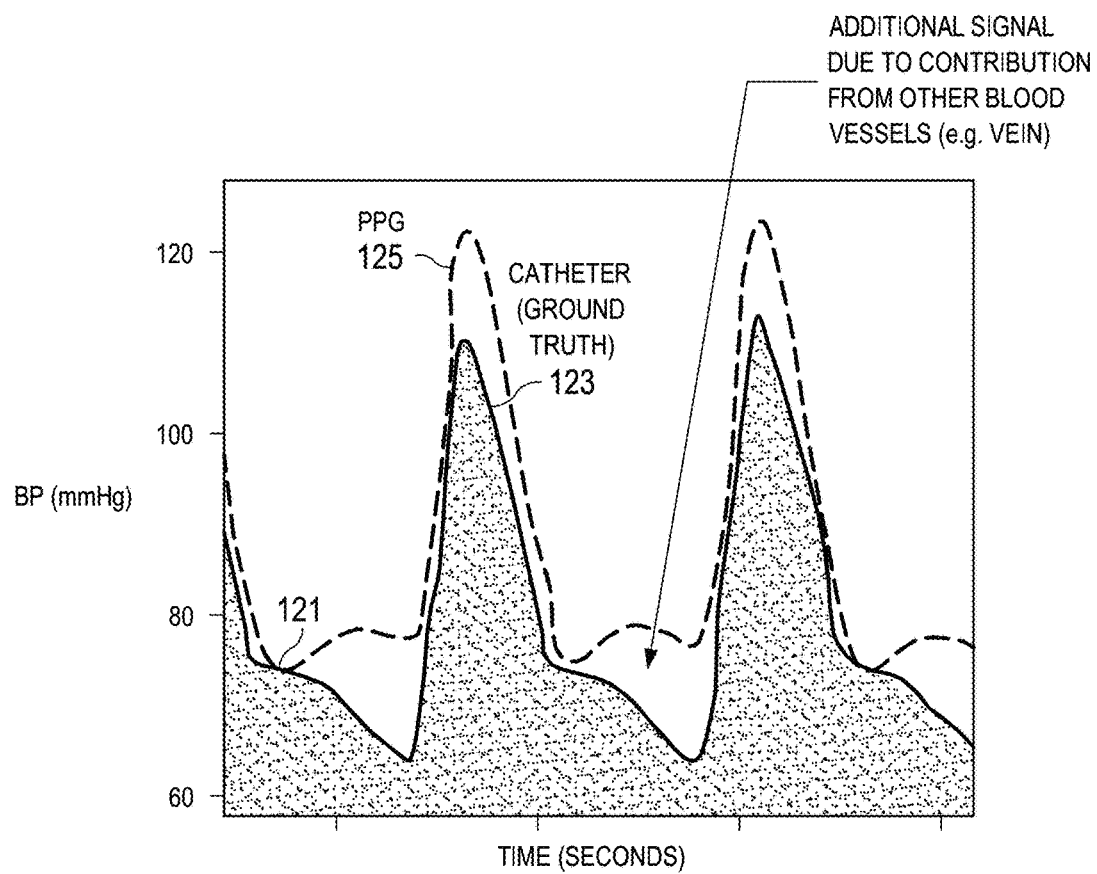
FIG. 1B shows an example of two superimposed graphs of blood pressure variation during cardiac cycles.

FIG. 1B shows an example of two superimposed graphs of blood pressure variation during cardiac cycles. The graph 123 corresponds to blood pressure measured by a catheter, which is a sufficiently reliable method to be considered a "ground truth" against which blood pressure estimation methods can be compared. In this example, the graph 125 corresponds to blood pressure estimated by a PPG-based method. In the example shown in FIG. 1B, the areas between the graph 123 and the graph 125 indicate the errors in blood pressure estimation according to the PPG-based method.

By comparing the heart rate waveform graphs 118 of FIG. 1A and the blood pressure graphs of FIG. 1B, one can appreciate that PPG-based blood pressure monitoring devices are not optimal because PPG superimposes data corresponding to the blood volume of all illuminated blood vessels, each of which exhibit different and time-shifted blood volume changes.

An alternative type of plethysmography that may be used to monitor blood pressure more accurately is photoacoustic plethysmography (PAPG). Like PPG, PAPG involves transmitting light onto an area of human tissue, such as tissue of a finger. However, PAPG involves measuring acoustic waves (as opposed to light) reflected from the tissue, and analyzing the reflected acoustic wave measurements to detect volumetric changes in the blood of the illuminated area.

Figure 1C:
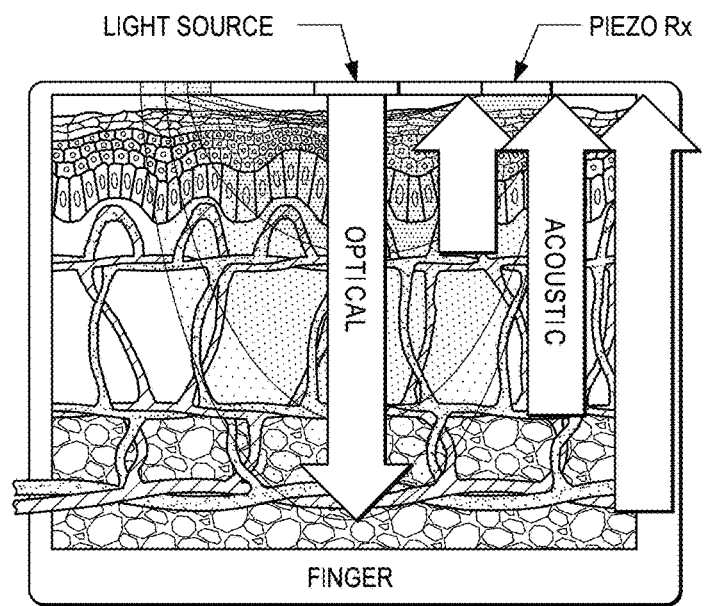
FIG. 1C shows an example of a blood pressure monitoring device based on photoacoustic plethysmography, which may be referred to herein as PAPG.

FIG. 1C shows an example of a blood pressure monitoring device based on PAPG. FIG. 1C shows the same examples of arteries, veins, arterioles, venules and capillaries inside the finger 115 that are shown in FIG. 1B. In some examples, the light source shown in FIG. 1C may be, or may include, one or more LEDs or laser diodes. In this example, as in FIG. 1A, the light source has transmitted light (in some examples, green, red, and/or near-infrared (NIR) light) that has penetrated the tissues of the finger 115 in an illuminated zone.

In the example shown in FIG. 1C, blood vessels (and components of the blood itself) are heated by the incident light from the light source and are emitting acoustic waves. In this example, the emitted acoustic waves include ultrasonic waves. According to this implementation, the acoustic wave emissions are being detected by an ultrasonic receiver, which is a piezoelectric receiver in this example. Photoacoustic emissions from the illuminated tissues, detected by the piezoelectric receiver, may be used to detect volumetric changes in the blood of the illuminated zone of the finger 115 that correspond to heart rate waveforms. In some examples, the ultrasonic receiver may correspond to the ultrasonic receiver 202 that is described below with reference to FIG. 2.

One important difference between the PPG-based system of FIG. 1A and the PAPG-based method of FIG. 1C is that the acoustic waves shown in FIG. 1C travel much more slowly than the reflected light waves shown in FIG. 1A. Accordingly, depth discrimination based on the arrival times of the acoustic waves shown in FIG. 1C is possible, whereas depth discrimination based on the arrival times of the light waves shown in FIG. 1A may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 2:
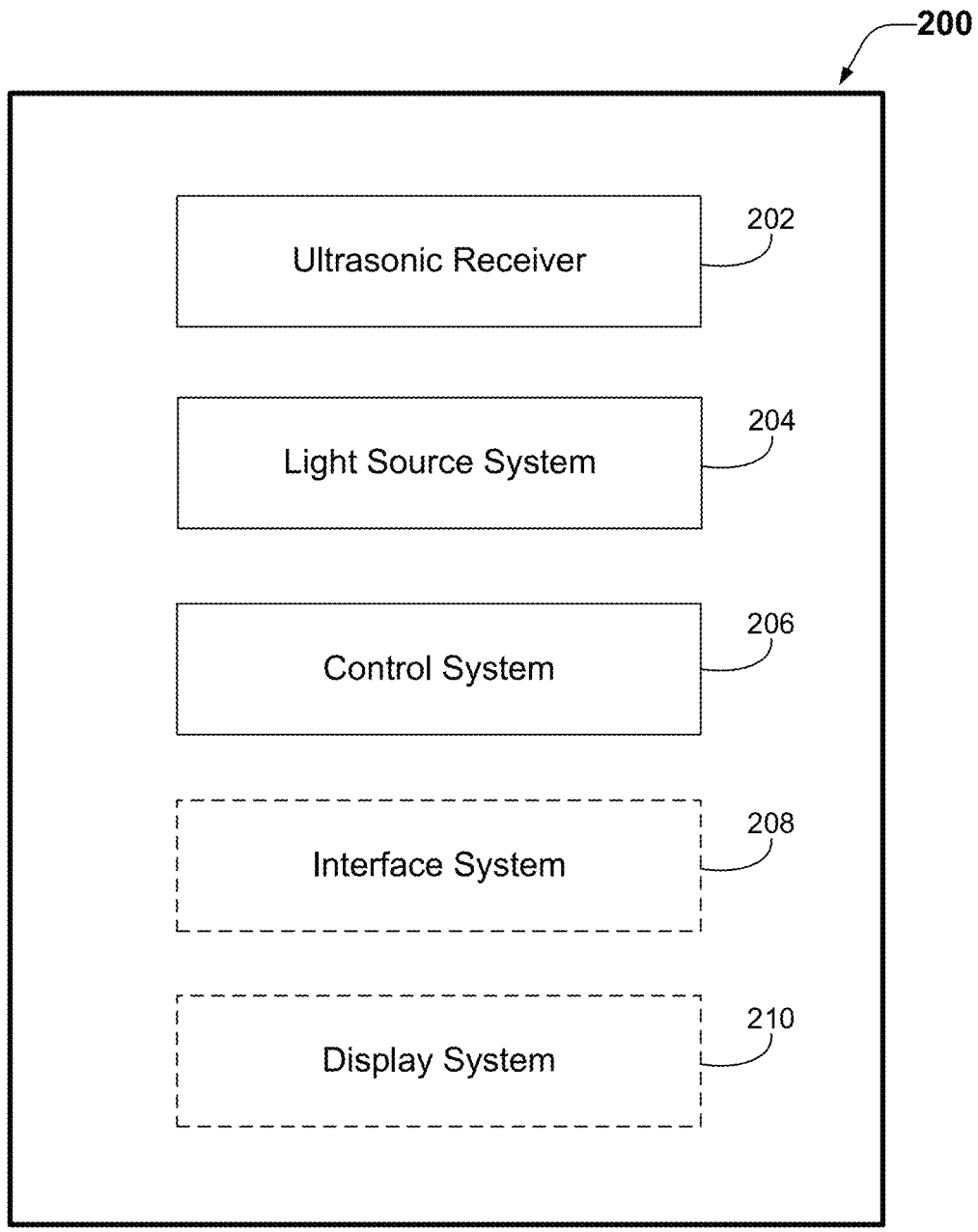
FIG. 2 is a block diagram that shows example components of an apparatus according to some examples.

FIG. 2 is a block diagram that shows example components of an apparatus according to some disclosed implementations. In this example, the apparatus 200 includes a biometric system. Here, the biometric system includes an ultrasonic receiver 202, a light source system 204 and a control system 206. Although not shown in FIG. 2, the apparatus 200 may include a substrate. In some examples, the apparatus 200 may include a platen. Some examples are described below. Some implementations of the apparatus 200 may include the interface system 208 and/or the display system 210.

Various examples of ultrasonic receivers 202 are disclosed herein, some of which may include, or be configured (or configurable) as, an ultrasonic transmitter and some of which may not. In some implementations the ultrasonic receiver 202 and an ultrasonic transmitter may be combined in an ultrasonic transceiver. In some examples, the ultrasonic receiver 202 may include a piezoelectric receiver layer, such as a layer of PVDF polymer or a layer of PVDF-TrFE copolymer. In some implementations, a single piezoelectric layer may serve as an ultrasonic receiver. In some implementations, other piezoelectric materials may be used in the piezoelectric layer, such as aluminum nitride (AlN) or lead zirconate titanate (PZT). The ultrasonic receiver 202 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the ultrasonic receiver 202 may be, or may include, an ultrasonic receiver array. In some examples, the apparatus 200 may include one or more separate ultrasonic transmitter elements. In some such examples, the ultrasonic transmitter(s) may include an ultrasonic plane-wave generator.

The light source system 204 may, in some examples, include an array of light-emitting diodes. In some implementations, the light source system 204 may include one or more laser diodes. According to some implementations, the light source system may include at least one infrared, red, green, blue, white or ultraviolet light-emitting diode. In some implementations, the light source system 204 may include one or more laser diodes. For example, the light source system 204 may include at least one infrared, red, green, blue, white or ultraviolet laser diode. In some implementations, the light source system 204 may include one or more organic LEDs (OLEDs).

In some implementations, the light source system 204 may be configured for emitting various wavelengths of light, which may be selectable in order to achieve greater penetration into biological tissue and/or to trigger acoustic wave emissions primarily from a particular type of material. For example, because near-infrared (near-IR) light is not as strongly absorbed by some types of biological tissue (such as melanin and blood vessel tissues) as relatively shorter wavelengths of light, in some implementations the light source system 204 may be configured for emitting one or more wavelengths of light in the near IR range, in order to obtain photoacoustic emissions from relatively deep biological tissues. In some such implementations the control system 206 may control the wavelength(s) of light emitted by the light source system 204 to be in the range of 750 to 850 nm, e.g., 808 nm. However, hemoglobin does not absorb near-IR light as much as hemoglobin absorbs light having shorter wavelengths, e.g., ultraviolet, violet, blue or green light. Near-IR light can produce suitable photoacoustic emissions from some blood vessels (e.g., 1 mm in diameter or larger), but not necessarily from very small blood vessels. In order to achieve greater photoacoustic emissions from blood in general and from smaller blood vessels in particular, in some implementations the control system 206 may control the wavelength(s) of light emitted by the light source system 204 to be in the range of 495 to 570 nm, e.g., 520 nm or 532 nm. Wavelengths of light in this range are more strongly absorbed by biological tissue and therefore may not penetrate the biological tissue as deeply, but can produce relatively stronger photoacoustic emissions in blood than near-IR light. In some examples the control system 206 may control the wavelength(s) of light emitted by the light source system 204 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver 202. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., as discussed in detail below) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose and/or blood oxygen within a blood vessel inside a target object such as a finger may be detected photoacoustically.

According to some implementations, the light source system 204 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 204 may be configured for emitting a plurality of light pulses at a pulse repetition frequency between about 1 MHz and about 100 MHz. Alternatively, or additionally, in some implementations the light source system 204 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 204 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 204. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 206 may include one or more general purpose single-or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 206 also may include (and/or be configured for communication with) one or more memory devices, such as one or more random access memory (RAM) devices, read-only memory (ROM) devices, etc. Accordingly, the apparatus 200 may have a memory system that includes one or more memory devices, though the memory system is not shown in FIG. 2. The control system 206 may be configured for receiving and processing data from the ultrasonic receiver 202, e.g., as described below. If the apparatus 200 includes an ultrasonic transmitter, the control system 206 may be configured for controlling the ultrasonic transmitter. In some implementations, functionality of the control system 206 may be partitioned between one or more controllers or processors, such as a dedicated sensor controller and an applications processor of a mobile device.

Some implementations of the apparatus 200 may include the interface system 208. In some examples, the interface system 208 may include a wireless interface system. In some implementations, the interface system 208 may include a user interface system, one or more network interfaces, one or more interfaces between the control system 206 and a memory system and/or one or more interfaces between the control system 206 and one or more external device interfaces (e.g., ports or applications processors).

According to some examples, the apparatus 200 may include a display system 210 that includes one or more displays. For example, the display system 210 may include one or more LED displays, such as one or more organic LED (OLED) displays.

The apparatus 200 may be used in a variety of different contexts, many examples of which are disclosed herein. For example, in some implementations a mobile device may include the apparatus 200. In some implementations, a wearable device may include the apparatus 200. The wearable device may, for example, be a bracelet, an armband, a wristband, a ring, a headband, an earbud or a patch.

Figure 3A:
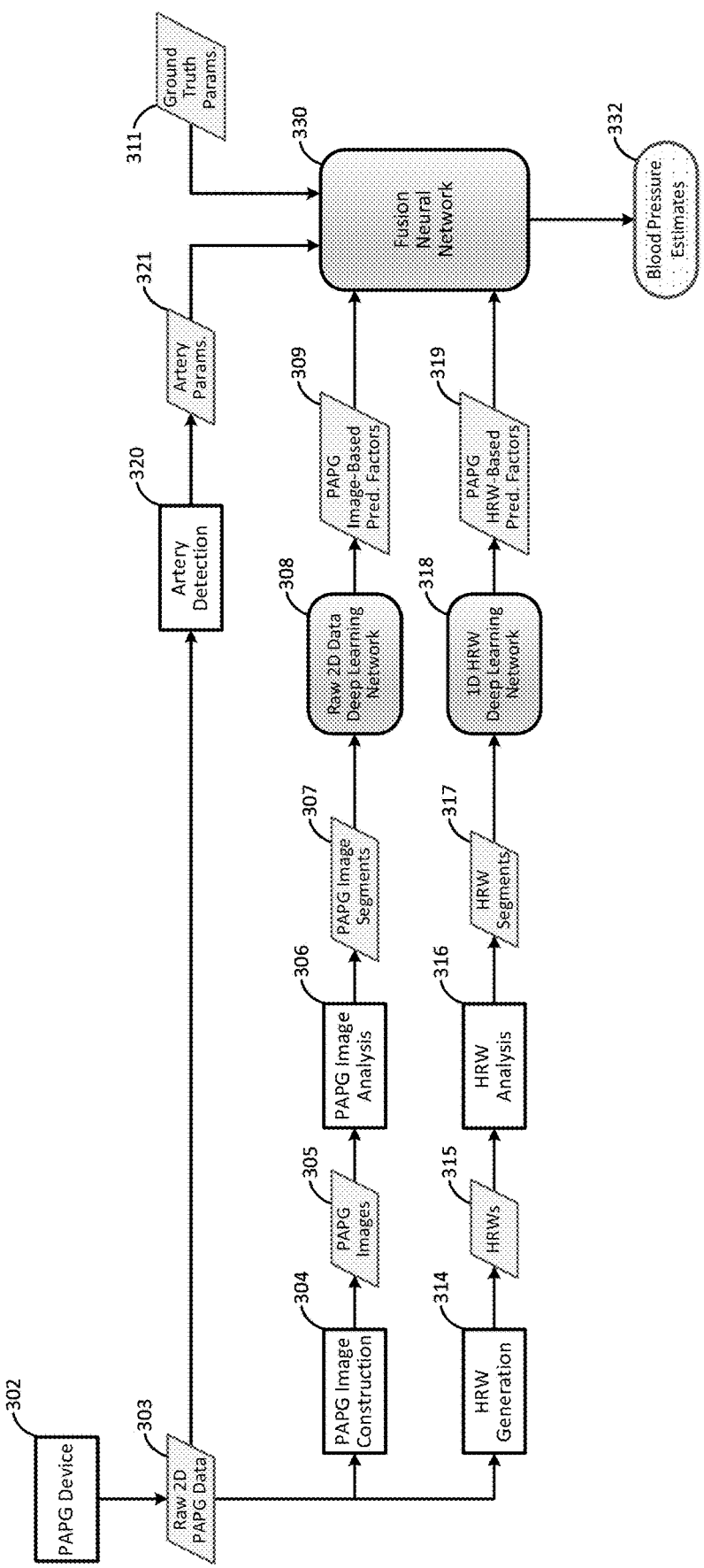
FIG. 3A is a block diagram that illustrates an example blood pressure estimation process according to some implementations.

FIG. 3A is a block diagram that illustrates an example blood pressure estimation process 300 according to some implementations. According to blood pressure estimation process 300, a PAPG device 302 can generate raw 2D PAPG data 303. According to some implementations, the PAPG device 302 can correspond to apparatus 200 of FIG. 2. The raw 2D PAPG data 303 can be used for PAPG image construction at 304, to create PAPG images 305. The PAPG images 305 can be subjected to PAPG image analysis at 306 to obtain PAPG image segments 307. The PAPG image analysis at 306 can include identifying regions of PAPG images 305 that correspond to various respective heart rate cycles, and each PAPG image segment 307 can be associated with a PAPG image region corresponding to a respective one of such heart rate cycles.

PAPG image segments 307 can be provided as inputs to a raw 2D data deep learning network 308. Based on PAPG image segments 307, the raw 2D data deep learning network 308 can determine PAPG image-based predictive factors 309. In various implementations, the PAPG image-based predictive factors 309 can include differential blood pressure estimates, absolute blood pressure estimates, or both. According to various implementations, PAPG image-based predictive factors 309 can include direct or indirect indicators of properties such as systolic artery diameter, diastolic artery diameter, arterial distention, arterial strain, arterial wave velocity (AWV), and pulse wave velocity (PWV).

In some implementations, the raw 2D data deep learning network 308 can normalize PAPG image segments 207 to obtain normalized PAPG image segments, and can determine PAPG image-based predictive factors 309 based on the normalized PAPG image segments. In some implementations, the normalization of PAPG image segments 307 can include amplitude normalization, time normalization, or both. In some implementations, the raw 2D data deep learning network 308 can transform the normalized PAPG image segments, such as via fast Fourier transform (FFT) or wavelet transform. In some implementations, the raw 2D data deep learning network 308 can determine PAPG image-based predictive factors 309 based on the normalized PAPG image segments (or transformations thereof) using a long short-term memory (LSTM) neural network or a convolutional neural network (CNN).

PAPG image-based predictive factors 309 can be provided as inputs to a fusion neural network 330. Based on PAPG image-based predictive factors 309, fusion neural network 330 can generate blood pressure estimates 332. In some implementations, blood pressure estimates 332 can be absolute blood pressures. In some implementations, fusion neural network 330 can generate blood pressure estimates 332 based on PAPG image-based predictive factors 309 and ground truth parameters 311. In some implementations, ground truth parameters 311 can indicate ground truth blood pressures, ground truth blood pressure differentials, or both for one or more heart rate cycles, and the fusion neural network 330 can use one or more such heart rate cycles as reference heart rate cycles for estimating blood pressure differentials associated with other heart rate cycles.

In some implementations, raw 2D PAPG data 303 can also be used for heart rate wave (HRW) generation at 314, to obtain heart rate waveforms 315. In some implementations, the heart rate waveform generation at 314 can include extracting HRW data from raw 2D PAPG data 303, bandpass-filtering the extracted HRW data to obtain filtered HRW data, and applying time-window averaging to the filtered HRW data to obtain averaged HRW data, and heart rate waveforms 315 can correspond to the averaged HRW data. The heart rate waveforms 315 can be subjected to heart rate waveform analysis at 316 to obtain heart rate waveform segments 317. The heart rate wave analysis at 316 can include identifying regions of heart rate waveforms 315 that correspond to various respective heart rate cycles, and each heart rate waveform segment 317 can be associated with a heart rate waveform region corresponding to a respective one of such heart rate cycles. In some implementations, the heart rate analysis at 316 can include performing HRW fiducial detection, including HRW peak and valley detection, based on averaged HRW data generated in conjunction with the heart rate waveform generation at 314. In some implementations, this can involve detecting systolic and diastolic valleys in the averaged HRW data. In some implementations, the heart rate analysis at 316 can include segmenting the heart rate waveforms 315 into heart rate waveform segments 317 based at least in part on output of the HRW fiducial detection, such as based at least in part on detection of systolic and diastolic valleys in the averaged HRW data.

Heart rate waveform segments 317 can be provided as inputs to a 1D heart rate waveform deep learning network 318. Based on heart rate waveform segments 317, the 1D heart rate waveform deep learning network 318 can determine PAPG HRW-based predictive factors 319. In various implementations, the PAPG HRW-based predictive factors 319 can include differential blood pressure estimates, absolute blood pressure estimates, or both. According to various implementations, PAPG HRW-based predictive factors 319 can include direct or indirect indicators of properties such as systolic artery diameter, diastolic artery diameter, arterial distention, arterial strain, arterial wave velocity (AWV), and pulse wave velocity (PWV).

In some implementations, the 1D heart rate waveform deep learning network 318 can normalize heart rate waveform segments 317 to obtain normalized heart rate wave segments, and can determine PAPG HRW-based predictive factors 319 based on the normalized heart rate wave segments. In some implementations, the normalization of heart rate wave segments 317 can include amplitude normalization, time normalization, or both. In some implementations, the 1D heart rate waveform deep learning network 318 can transform the normalized heart rate wave segments, such as via FFT or wavelet transform. In some implementations, the 1D heart rate waveform deep learning network 318 can determine PAPG HRW-based predictive factors 319 based on the normalized heart rate wave segments (or transformations thereof) using a long short-term memory (LSTM) neural network or a convolutional neural network (CNN).

In some implementations, PAPG HRW-based predictive factors 319 can be provided along with PAPG image-based predictive factors 309 as inputs to fusion neural network 330. In some implementations, fusion neural network 330 can generate blood pressure estimates 332 based on PAPG image-based predictive factors 309, PAPG HRW-based predictive factors 319, and ground truth parameters 311. In some implementations, based on raw 2D PAPG data 303, artery detection may be performed at 320 to determine artery parameters 321. In some implementations, artery parameters 321 may include artery diameter parameters, artery distension parameters, or both. In some implementations, fusion neural network 330 can generate blood pressure estimates 332 based on PAPG image-based predictive factors 309, PAPG HRW-based predictive factors 319, ground truth parameters 311, and artery parameters 321.

In some implementations, the control system 206 of apparatus 200 of FIG. 2 can perform the operations at one or more of blocks 304, 306, 308, 314, 316, 318, 320, and 330 in FIG. 3A. In some implementations, control system 206 can perform the operations at some of blocks 304, 306, 308, 314, 316, 318, 320, and 330, while the operations at others of blocks 304, 306, 308, 314, 316, 318, 320, and 330 can be performed by a control system of another device. In some implementations, for example, control system 206 can perform the operations at some of blocks 304, 306, 308, 314, 316, 318, 320, and 330 to obtain data, parameters, and/or information that is passed to another device via interface system 208 for use by that other device to perform the operations at others of blocks 304, 306, 308, 314, 316, 318, 320, and 330. In some implementations, the other device can be, for example, a computing device, a mobile health device, a mobile communication device, or another type of device, such as any of the examples listed above. In some implementations, the other device can be a wearable device.

Figure 3B:
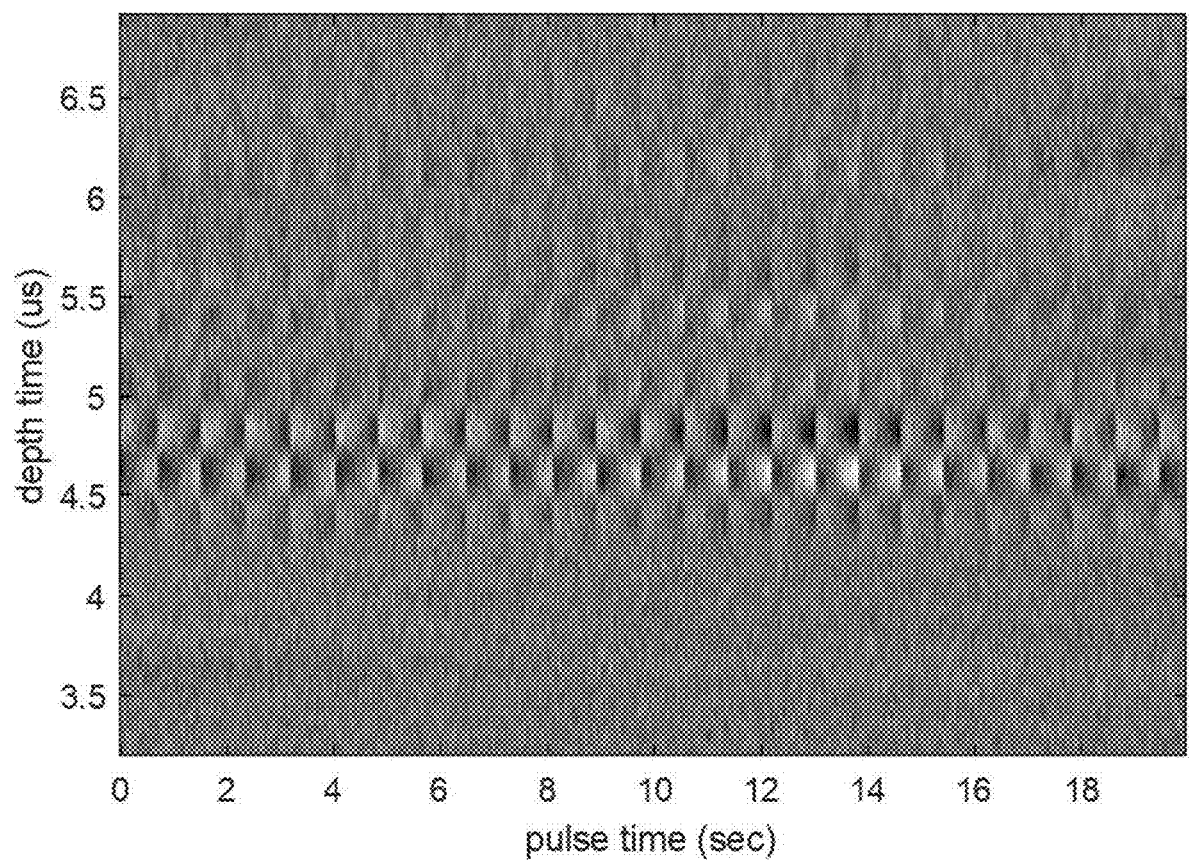
FIG. 3B illustrates an example plethysmography image according to aspects of the disclosure.

FIG. 3B depicts an example plethysmography image 350 according to aspects of the disclosure. Plethysmography image 350 may be representative of, for instance, a PAPG image 305 constructed in conjunction with implementation of blood pressure estimation scheme 300 of FIG. 3A according to some examples. A horizontal axis provides scale for a pulse time dimension of plethysmography image 350 (in units of seconds in the depicted example). A vertical axis provides scale for a depth time dimension of plethysmography image 350 (in units of microseconds (μs) in the depicted example). The depth time dimension can represent arterial diameter, distension, and strain, while the pulse time dimension can represent arterial wave velocity (AWV) and pulse wave velocity (PWV). The intensity at a given point in plethysmography image 350 can correspond to an amount of acoustic energy proportional to an amount of light absorbed by arterial hemoglobin.

Figure 4:
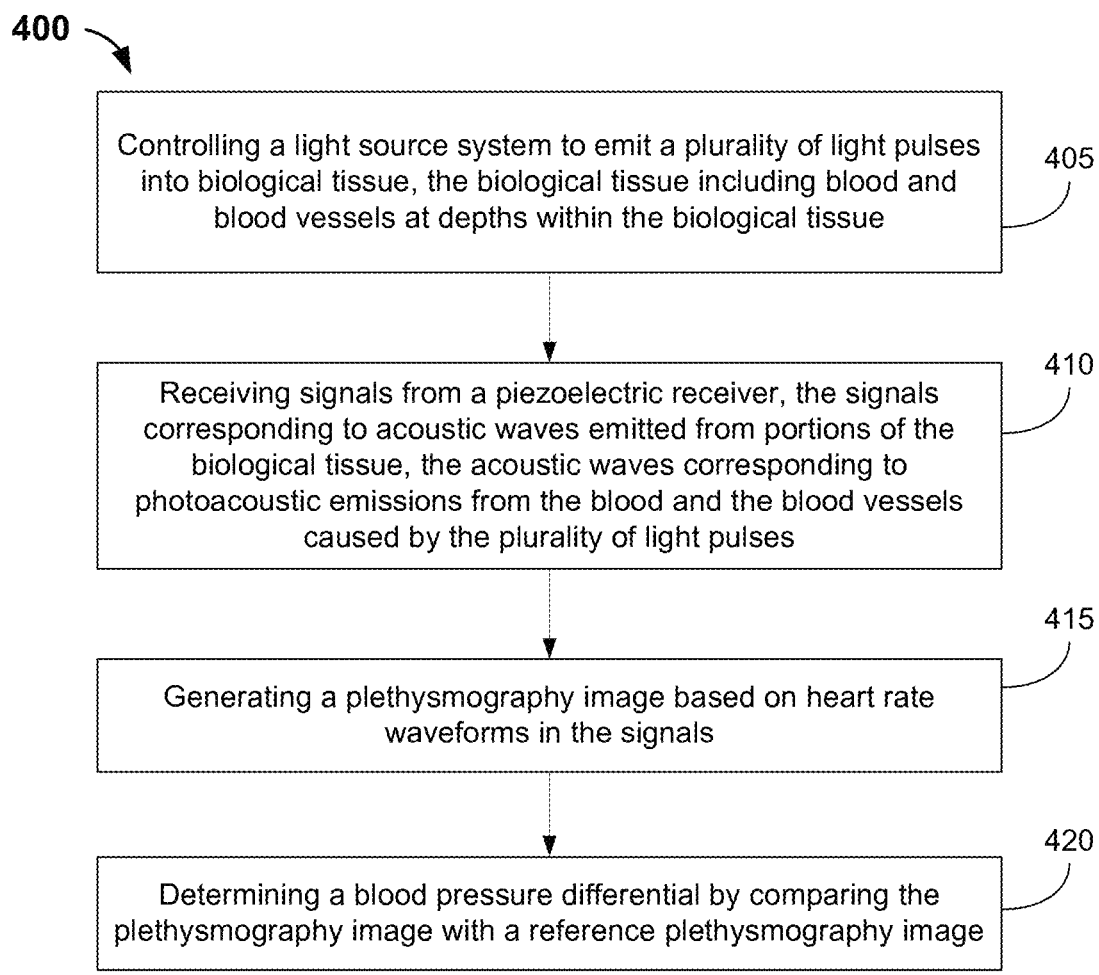
FIG. 4 illustrates an example method according to aspects of the disclosure.

FIG. 4 illustrates an example method 400 according to aspects of the disclosure. Method 400 may be representative of operations that may, for instance, be performed by apparatus 200 of FIG. 2 in conjunction with implementation of blood pressure estimation scheme 300 of FIG. 3A according to some examples. In various implementations, method 400 may include more or fewer blocks than indicated. Moreover, the blocks of method 400 are not necessarily performed in the order indicated. In some instances, one or more of the blocks shown in FIG. 4 may be performed concurrently.

According to method 400, a light source system may be controlled by a control system at 405 to emit a plurality of light pulses into biological tissue, and the biological tissue may include blood and blood vessels at depths within the biological tissue. For example, control system 206 of apparatus 200 of FIG. 2 may control light source system 204 to emit a plurality of light pulses into tissue of a finger, as depicted in FIG. 1C. In some examples, the light source system can be configured for emitting a plurality of light pulses at a pulse repetition frequency. In some such examples, the pulse repetition frequency may be in a range between, or including, 10 Hz and 1 MHz.

In some implementations, the control system may be configured for selecting one or more wavelengths of light for the plurality of light pulses, e.g., as described above. According to some examples, the control system may be configured for selecting a light intensity associated with one or more selected wavelengths. For example, the control system may be configured for selecting one or more wavelengths of light and light intensities associated with each selected wavelength to generate acoustic wave emissions from one or more portions of the target object. In some examples, the control system may be configured for selecting the one or more wavelengths of light to evaluate one or more characteristics of the target object, e.g., to evaluate blood oxygen levels. In some examples, block 405 may involve controlling the light source system to emit light that is transmitted through a substrate and/or other layers of an apparatus such as the apparatus 200.

At 410, signals may be received from a piezoelectric receiver that correspond to acoustic waves emitted from portions of the biological tissue into which the plurality of light pulses was emitted at 405, where the acoustic waves correspond to photoacoustic emissions from the blood and the blood vessels caused by the plurality of light pulses. For example, control system 206 of apparatus 200 of FIG. 2 may receive signals from ultrasonic receiver 202 (which may be a piezoelectric receiver) that correspond to acoustic waves emitted from portions of the finger tissue into which light pulses are emitted in FIG. 1C, and the acoustic waves may correspond to photoacoustic emissions from blood and blood vessels included at depths within the finger tissue. In some examples, an ultrasonic receiver (such as ultrasonic receiver 202 of FIG. 2) may be, or include, the piezoelectric receiver. In some examples, a target object (such as a digit, a wrist or another body part) that includes the biological tissue may be positioned on a surface of the ultrasonic receiver or positioned on a surface of a device that includes the ultrasonic receiver. In some examples, one or more coatings or acoustic matching layers (e.g., for matching the acoustic impedance of human skin) may reside on a surface of the ultrasonic receiver or a surface of a device that includes the ultrasonic receiver (e.g., a surface of a cover glass or a platen of the device).

At 415, a plethysmography image may be generated based on heart rate waveforms in the signals. For example, control system 206 of apparatus 200 of FIG. 2 may implement PAPG image constructor 304 of FIG. 3A, which may generate a PAPG image 305 based on raw 2D PAPG data 303 in signals that control system 206 receives from ultrasonic receiver 202. In some examples, the plethysmography image can include a depth time dimension and a pulse time dimension.

At 420, a blood pressure differential may be determined by comparing the plethysmography image generated at 415 with a reference plethysmography image. For example, control system 206 of apparatus 200 of FIG. 2 may implement PAPG image analyzer 306 and raw 2D data DLN 308, which may work in combination to determine a blood pressure differential by comparing a plethysmography image generated by PAPG image constructor 304 with a reference plethysmography image. In some examples, the blood pressure differential may be displayed on a display. In some examples, the reference plethysmography image may correspond to a first heart rate cycle and the plethysmography image may correspond to a second heart rate cycle. In some examples, the reference plethysmography image can be generated based on a first raw plethysmography signal, and the plethysmography image can be generated based on a second raw plethysmography signal. In some examples, the plethysmography image and the reference plethysmography image can be time-normalized.

In some examples, a ground truth blood pressure can be identified, and an absolute blood pressure can be determined based on the ground truth blood pressure and the blood pressure differential. In some examples, the absolute blood pressure can be displayed on a display. In some examples, the ground truth blood pressure can be a cuff-based blood pressure.

Figure 5A:
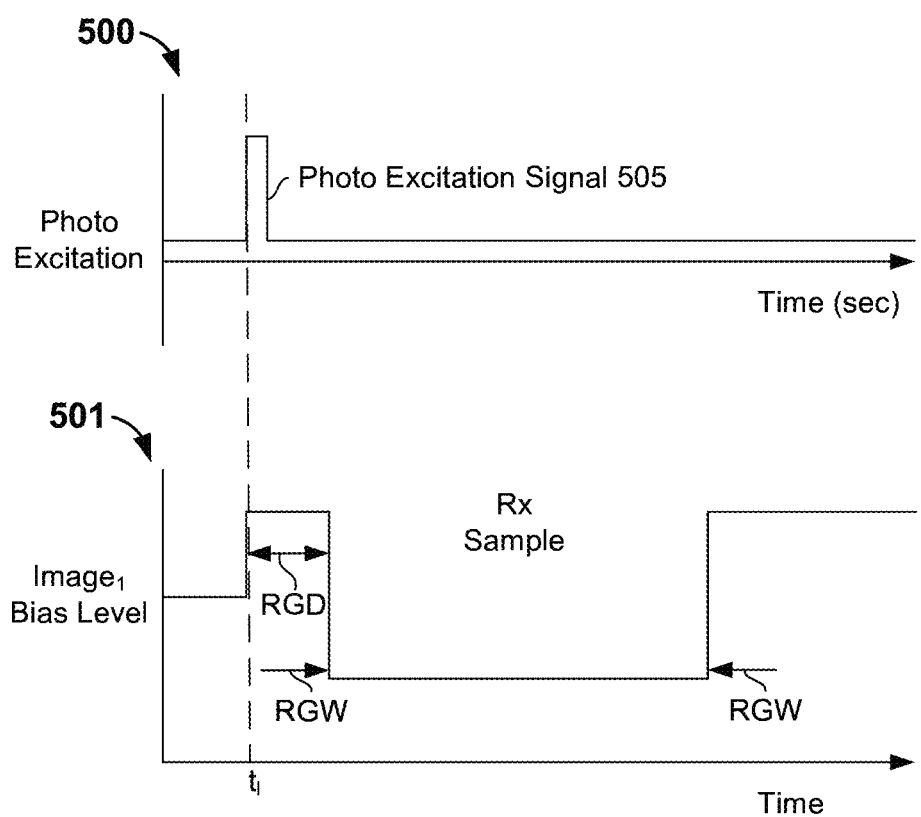
FIG. 5A shows an example of a range-gate window (RGW) selected to receive acoustic waves emitted from a range of different depths.

In some examples, the control system may be configured for discriminating between vein heart rate waveforms and artery heart rate waveforms by obtaining depth-discriminated signals. FIG. 5A shows an example of a range-gate window (RGW) selected to receive acoustic waves emitted from a range of different depths. The acquisition time delay or range gate delay (which is labeled "RGD" in FIG. 5B) is measured from the beginning time $t_1$ of the photo-excitation signal 505 shown in graph 500. The RGD may, for example, be selected to correspond with the time required for photoacoustic emissions from a shallowest target of interest to reach a receiver, e.g., as described below with reference to FIGS. 6A and 6B. Accordingly, the RGD may depend on the particular arrangement of the apparatus being used to receive the photoacoustic emissions, including the thickness of the layer(s) between the target object and the receiver and the speed of sound of the layer(s) between the target object and the receiver. The graph 501 depicts a time after RGD during which emitted acoustic waves may be received and sampled by an ultrasonic receiver during an acquisition time window (also known as a range-gate window or a range-gate width) of RGW. In some implementations, the RGW may be 10 microseconds. Other implementations may have larger or smaller RGWs.

In some examples, depth-discriminated signals may be obtained by a process of partitioning the acoustic waves received during the RGW into a plurality of smaller time windows. Each of the time windows may correspond to a depth range inside the target object from which the acoustic waves are received. In some examples, the depth range or thickness of each layer may be 0.5 mm. Assuming a speed of sound of 1.5 mm/microsecond, each 0.5 mm layer would correspond to a time slot of approximately 0.33 microseconds. However, the depth range may vary according to the particular implementation.

According to some alternative examples, receiving the signals from the piezoelectric receiver involves obtaining depth-discriminated signals by applying first through $N^{th}$ acquisition time delays and receiving first through $N^{th}$ signals during first through $N^{th}$ acquisition time windows, each of the first through $N^{th}$ acquisition time windows occurring after a corresponding one of the first through $N^{th}$ acquisition time delays, wherein N is an integer greater than one. The control system may be configured for determining the first subset of detected heart rate waveforms and the second subset of detected heart rate waveforms based, at least in part, on the depth-discriminated signals.

Figure 5B:
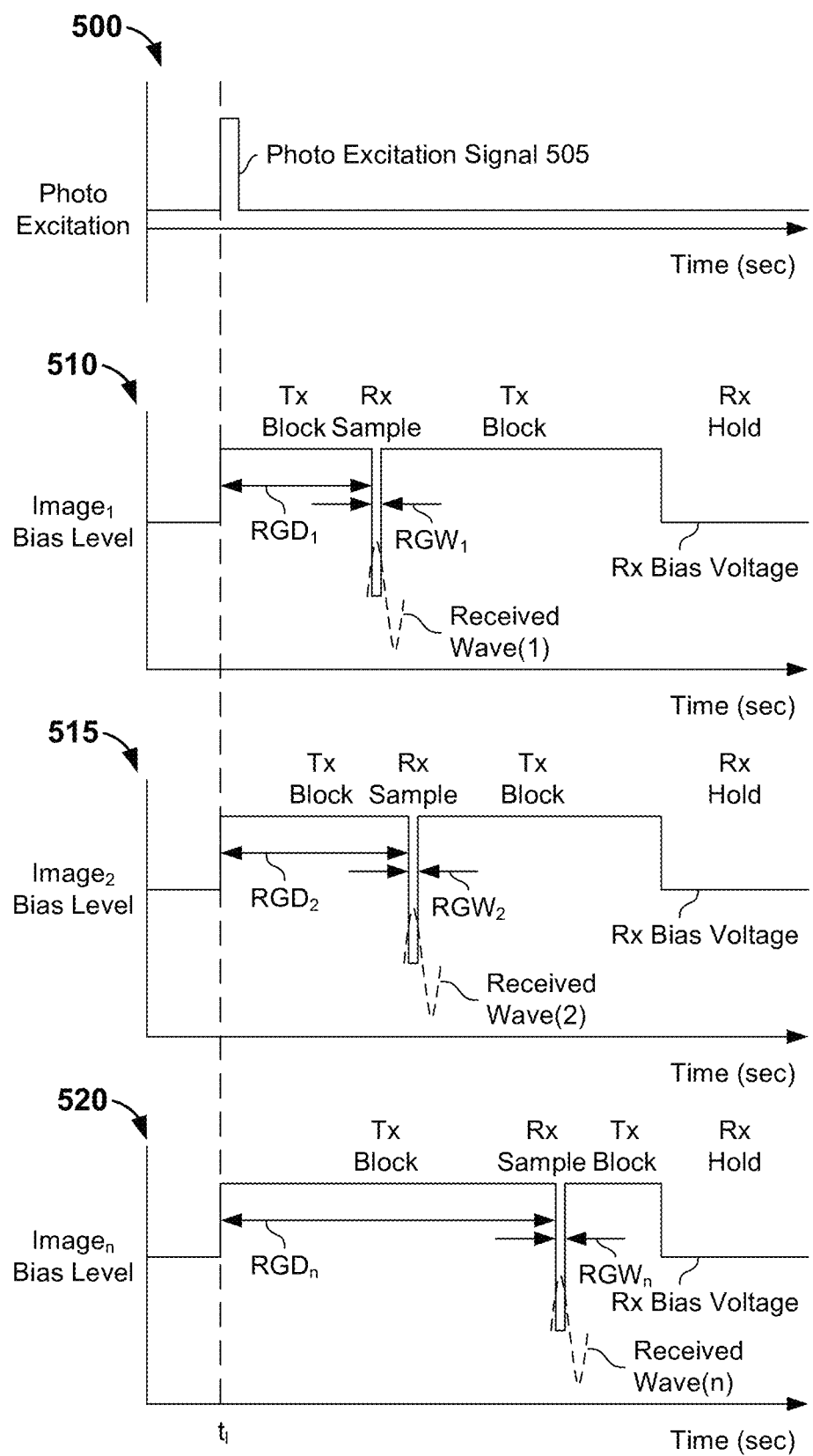
FIG. 5B shows examples of multiple acquisition time delays being selected to receive acoustic waves emitted from different depths.

FIG. 5B shows examples of multiple acquisition time delays being selected to receive acoustic waves emitted from different depths. In these examples, each of the acquisition time delays (which are labeled range-gate delays or RGDs in FIG. 5B) is measured from the beginning time $t_1$ of the photo-excitation signal 505 shown in graph 500. The graph 510 depicts emitted acoustic waves (received wave (1) is one example) that may be received by an ultrasonic sensor array at an acquisition time delay $RGD_1$ and sampled during an acquisition time window (also known as a range-gate window or a range-gate width) of $RGW_1$. Such acoustic waves will generally be emitted from a relatively shallower portion of a target object proximate, or positioned upon, a platen of the biometric system.

Graph 515 depicts emitted acoustic waves (received wave (2) is one example) that are received by the ultrasonic sensor array at an acquisition time delay $RGD_2$ (with $RGD_2 > RGD_1$) and sampled during an acquisition time window of $RGW_2$. Such acoustic waves will generally be emitted from a relatively deeper portion of the target object.

Graph 520 depicts emitted acoustic waves (received wave (n) is one example) that are received at an acquisition time delay $RGD_n$ (with $RGD_n > RGD_2 > RGD_1$) and sampled during an acquisition time window of $RGW_n$. Such acoustic waves will generally be emitted from a still deeper portion of the target object. Range-gate delays are typically integer multiples of a clock period. A clock frequency of 128 MHz, for example, has a clock period of 7.8125 nanoseconds, and RGDs may range from under 10 nanoseconds to over 2000 nanoseconds. Similarly, the range-gate widths may also be integer multiples of the clock period, but are often much shorter than the RGD (e.g. less than about 50 nanoseconds) to capture returning signals while retaining good axial resolution. In some implementations, the acquisition time window (e.g. RGW) may be between 175 nanoseconds to 320 nanoseconds or more. In some examples, the RGW may be more or fewer nanoseconds, e.g., in the range of 25 nanoseconds to 1000 nanoseconds.

Figure 6A:
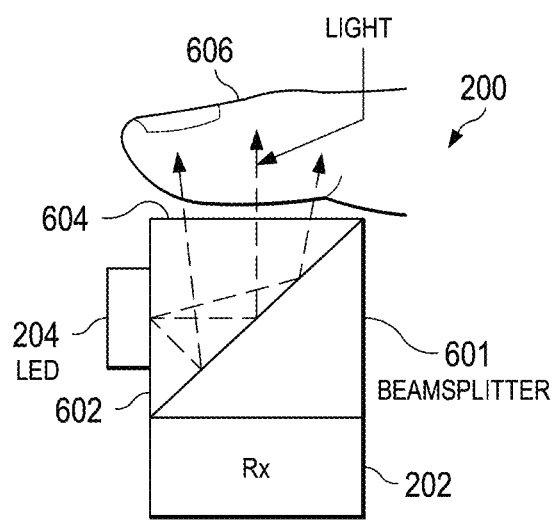
FIGS. 6A and 6B show examples of an apparatus configured to receive acoustic waves emitted from different depths.
Figure 6B:
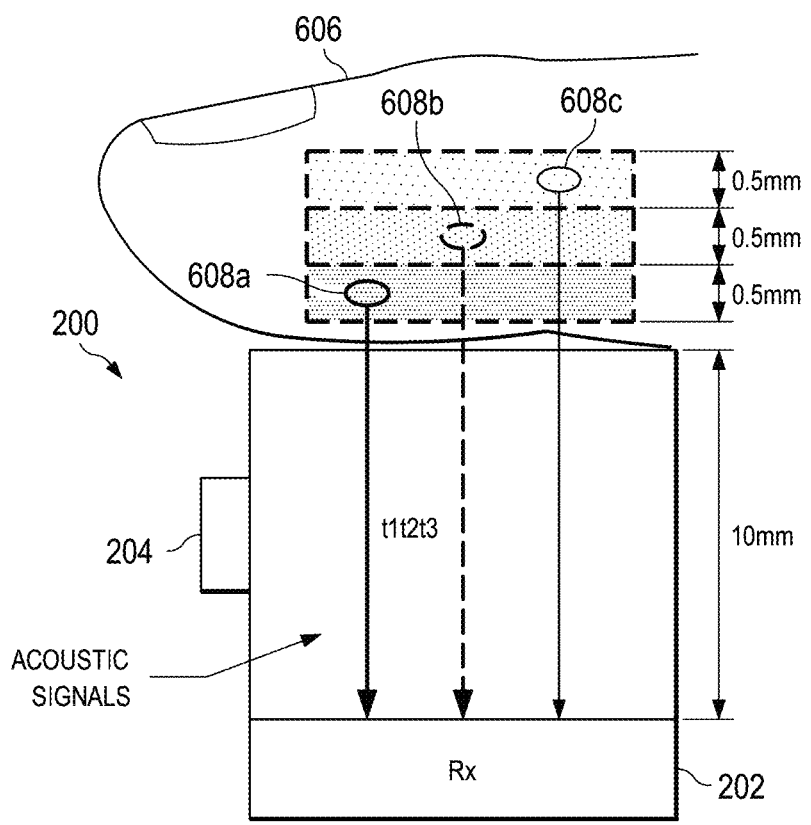

FIGS. 6A and 6B show examples of an apparatus configured to receive acoustic waves emitted from different depths. The apparatus shown in FIGS. 6A and 6B is an example of the apparatus 200 that is shown in FIG. 2. As with the other implementations shown and described herein, the types of elements, the arrangement of the elements and the dimensions of the elements illustrated in FIGS. 6A and 6B are merely shown by way of example.

According to this example, the apparatus 200 includes an ultrasonic receiver 202, a light source system 204 (which includes an LED in this example) and a control system (which is not shown in FIGS. 6A and 6B). According to this implementation, the apparatus 200 includes a beamsplitter 601 onto a side 602 to which the LED is mounted. In this instance, a finger 606 rests upon an adjacent side 604 of the beamsplitter 601.

FIG. 6A shows light emitted from the light source system 204, part of which is reflected by the beamsplitter 601 and enters the finger 606. The range gate delay for this implementation and other implementations may, for example, be selected to correspond with the time required for photoacoustic emissions from a shallowest target of interest to reach a receiver. For example, in one configuration of the apparatus 200 which uses a 12.7 mm beamsplitter between the finger 606 and the ultrasonic receiver 202 (RX in FIG. 6A), the finger surface signal will arrive at the time it takes the acoustic waves to travel through the entire beamsplitter. Using the speed of sound of borosilicate glass of 5500 m/s as an approximate speed of sound for the beamsplitter and with the beamsplitter size of 12.7 mm, this time becomes 12.7 mm/5500 m/s or 2.3 us. Therefore, a range gate delay of 2.3 µs corresponds to the surface of the finger 606. To travel 1 mm into the finger 606, for example, using the speed of sound for tissue now of 1.5 mm/us, this time becomes 1 mm/1.5 mm/µs or ~0.67 µs. Therefore, a range gate delay of ~2.97 µs (2.3 µs+0.67 µs) would cause the ultrasonic receiver 202 to begin sampling acoustic waves reflected from a depth of approximately 1 mm below the outer surface of the finger 606.

FIG. 6B shows acoustic signals corresponding to photoacoustic emissions from tissues (e.g., blood and blood vessels) inside the finger 606, caused by the light that entered the finger 606. In the example shown in FIG. 6B, the acoustic signals originate from different depths (depths 608a, 608b and 608c) within the finger 606. Accordingly, the travel times t1, t2 and t3, from the depths 608a, 608b and 608c, respectively, to the ultrasonic receiver 202, are also different: in this instance, t3>t2>t1. Therefore, multiple acquisition time delays may be selected to receive acoustic waves emitted from the depths 608a, 608b and 608c, e.g., as shown in FIG. 5B and described above.

Figure 7:
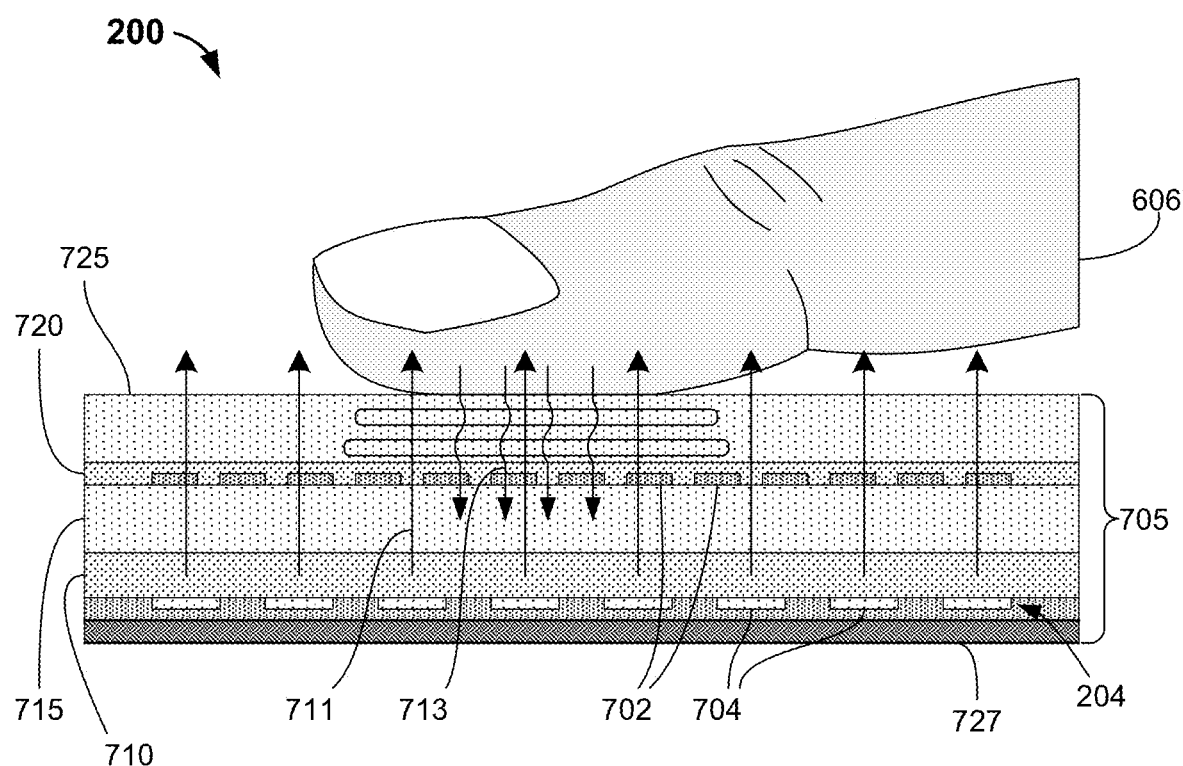
FIG. 7 shows an example of a cross-sectional view of an apparatus capable of performing the method of FIG. 4.

FIG. 7 shows an example of a cross-sectional view of an apparatus capable of performing the method of FIG. 4. The apparatus 200 shown in FIG. 7 is another example of the apparatus 200 that is described above with reference to FIG. 2. As with the other implementations shown and described herein, the types of elements, the arrangement of the elements and the dimensions of the elements illustrated in FIG. 7 are merely shown by way of example.

FIG. 7 shows an example of a target object (the finger 606, in this instance) being illuminated by incident light and subsequently emitting acoustic waves. In this example, the apparatus 200 includes a light source system 204, which may include an array of light-emitting diodes and/or an array of laser diodes. In some implementations, the light source system 204 may be capable of emitting various wavelengths of light, which may be selectable to trigger acoustic wave emissions primarily from a particular type of material. In some instances, the incident light wavelength, wavelengths and/or wavelength range(s) may be selected to trigger acoustic wave emissions primarily from a particular type of material, such as blood, blood vessels, other soft tissue, or bones. To achieve sufficient image contrast, light sources 704 of the light source system 204 may need to have a higher intensity and optical power output than light sources generally used to illuminate displays. In some implementations, light sources with light output of 1-100 millijoules or more per pulse, e.g., 10 millijoules per pulse, with pulse widths in the range of 100 nanoseconds to 600 nanoseconds, may be suitable. In some implementations, the pulse width of the emitted light may be between 10 nanoseconds and 700 nanoseconds.

In this example, incident light 711 has been transmitted from the light sources 704 of the light system 204 through a sensor stack 705 and into an overlying finger 606. The various layers of the sensor stack 705 may include one or more substrates of glass or other material such as plastic or sapphire that is substantially transparent to the light emitted by the light source system 204. In this example, the sensor stack 705 includes a substrate 710 to which the light source system 204 is coupled, which may be a backlight of a display according to some implementations. In alternative implementations, the light source system 204 may be coupled to a front light. Accordingly, in some implementations the light source system 204 may be configured for illuminating a display and the target object.

In this implementation, the substrate 710 is coupled to a thin-film transistor (TFT) substrate 715 for the ultrasonic receiver 202, which includes an array of sensor pixels 702 in this example. According to this example, a piezoelectric receiver layer 720 overlies the sensor pixels 702 of the ultrasonic receiver 202 and a platen 725 overlies the piezoelectric receiver layer 720. Accordingly, in this example the apparatus 200 is capable of transmitting the incident light 711 through one or more substrates of the sensor stack 705 that include the ultrasonic receiver 202 with substrate 715 and the platen 725 that may also be viewed as a substrate. In some implementations, sensor pixels 702 of the ultrasonic receiver 202 may be transparent, partially transparent or substantially transparent, such that the apparatus 200 may be capable of transmitting the incident light 711 through elements of the ultrasonic receiver 202. In some implementations, the ultrasonic receiver 202 and associated circuitry may be formed on or in a glass, plastic or silicon substrate.

According to some implementations, the apparatus 200 may include an ultrasonic transmitter 727, such as the ultrasonic transmitter 727 that is shown in FIG. 7. The ultrasonic transmitter may or may not be part of the ultrasonic receiver 202, depending on the particular implementation. In some examples, the ultrasonic receiver 202 may include PMUT or CMUT elements that are capable of transmitting and receiving ultrasonic waves, and the piezoelectric receiver layer 720 may be replaced with an acoustic coupling layer. In some examples, the ultrasonic receiver 202 may include an array of pixel input electrodes and sensor pixels formed in part from TFT circuitry, an overlying piezoelectric receiver layer 720 of piezoelectric material such as PVDF or PVDF-TrFE, and an upper electrode layer positioned on the piezoelectric receiver layer sometimes referred to as a receiver bias electrode. In the example shown in FIG. 7, at least a portion of the apparatus 200 includes an ultrasonic transmitter 727 that can function as a plane-wave ultrasonic transmitter. The ultrasonic transmitter 727 may, for example, include a piezoelectric transmitter layer with transmitter excitation electrodes disposed on each side of the piezoelectric transmitter layer.

Here, the incident light 711 causes optical excitation within the finger 606 and resultant acoustic wave generation. In this example, the generated acoustic waves 713 include ultrasonic waves. Acoustic emissions generated by the absorption of incident light may be detected by the ultrasonic receiver 202. A high signal-to-noise ratio may be obtained because the resulting ultrasonic waves are caused by optical stimulation instead of by reflection of transmitted ultrasonic waves.

In this example, the apparatus 200 includes a control system, although the control system is not shown in FIG. 7. According to some examples, the control system may be configured for discriminating between vein heart rate waveforms and artery heart rate waveforms by obtaining depth-discriminated signals. According to some such examples, receiving the signals from the piezoelectric receiver involves obtaining depth-discriminated signals by selecting an acquisition time window to receive acoustic waves emitted from a range of different depths within a target object, such as a finger, a wrist, an ear, etc. In some examples, depth-discriminated signals may be obtained by a process of partitioning the acoustic waves received during the RGW into a plurality of smaller time windows, e.g., as described above. Each of the time windows may correspond to a depth range inside the target object from which the acoustic waves are received. According to some alternative examples, receiving the signals from the piezoelectric receiver involves obtaining depth-discriminated signals by applying first through $N^{th}$ acquisition time delays and receiving first through $N^{th}$ signals during first through $N^{th}$ acquisition time windows, each of the first through $N^{th}$ acquisition time windows occurring after a corresponding one of the first through $N^{th}$ acquisition time delays, wherein N is an integer greater than one. The control system may be configured for determining vein heart rate waveforms and artery heart rate waveforms based, at least in part, on the depth-discriminated signals.

Figure 8:
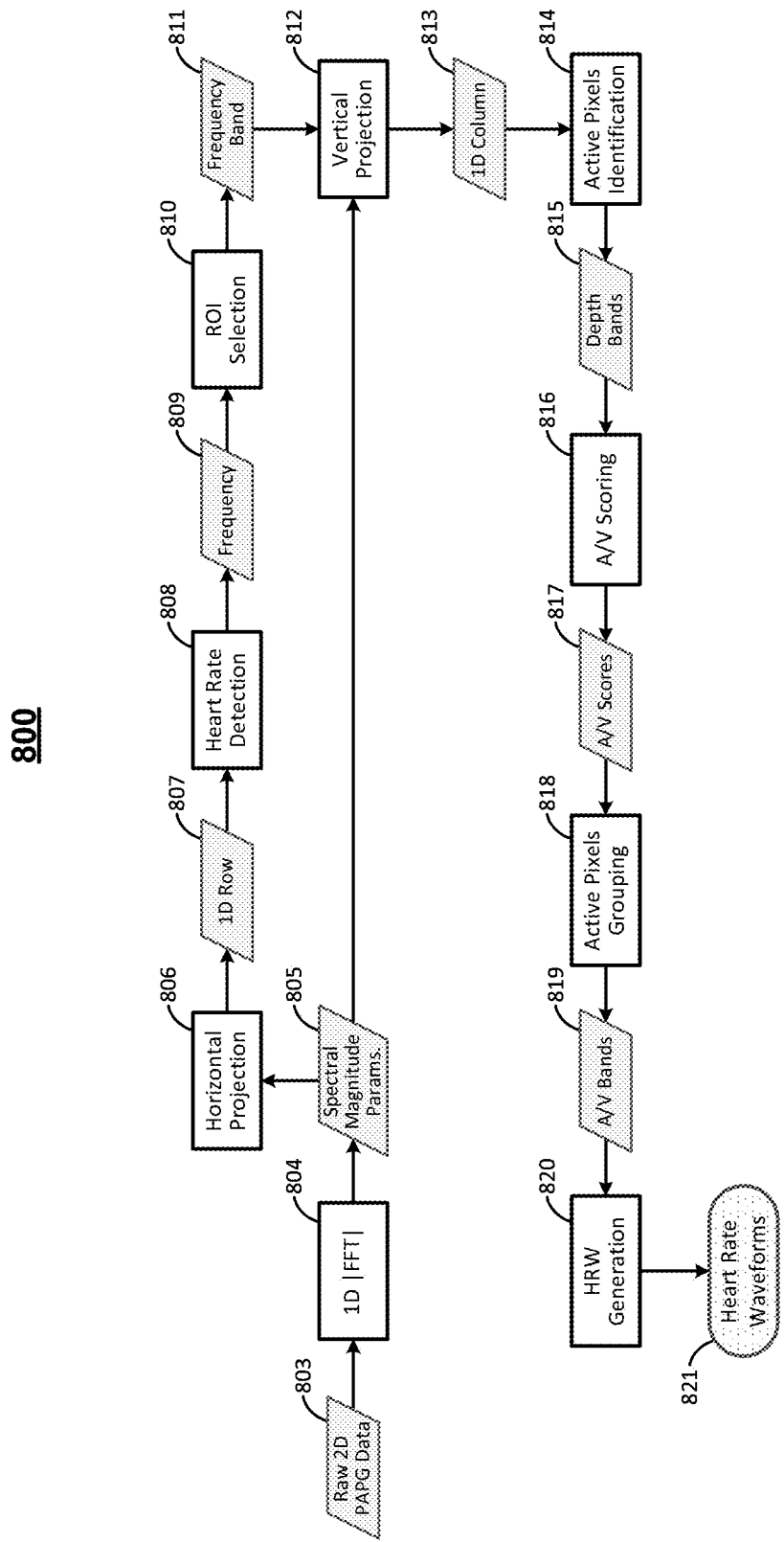
FIG. 8 is a block diagram that illustrates an example heart rate wave generation process according to some implementations.

FIG. 8 is a block diagram that illustrates an example heart rate wave generation process 800 according to some implementations. According to heart rate wave generation process 800, raw 2D PAPG data 803 can be subjected to one-dimensional fast Fourier transformation at 804 to obtain spectral magnitude parameters 805 associated with raw 2D PAPG data 803. Based on the spectral magnitude parameters 805, horizontal projection can be conducted at 806 to obtain a 1D row 807. Heart rate detection can be performed at 808 to identify a frequency 809 based on the 1D row 807. The frequency 809 can serve as a basis for region-of-interest (ROI) selection at 810, which can result in selection of a frequency band 811. Based on the spectral magnitude parameters 805 and the frequency band 811, vertical projection can be conducted at 812 to obtain a 1D column 813. Active pixels identification can be performed at 814 to determine depth bands 815 based on 1D column 813. Depth bands 815 can serve as input to artery/vein (A/V) scoring at 816, which can yield A/V scores 817. Active pixels grouping at 818 can determine A/V bands 819 based on A/V scores 817. Heart rate wave generation can be conducted at 820 in accordance with the determination of A/V bands 819, to produce heart rate waveforms 821.

In some implementations, some or all of the components of apparatus 200 of FIG. 2 may be arranged, assembled or otherwise included within a single housing of a single ambulatory monitoring device. In some examples, the housing and other components of the ambulatory monitoring device can be configured such that when the ambulatory monitoring device is affixed or otherwise physically coupled to a subject, light source system 204 will emit light pulses into tissue along a stretch of an artery along which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In various implementations, the housing and coupling mechanism can enable full ambulatory use. In other words, some implementations of the wearable monitoring devices described herein are noninvasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device can facilitate and enable long-term wearing and monitoring (for example, over days, weeks or a month or more without interruption) of one or more biological characteristics of interest to obtain a better picture of such characteristics over extended durations of time, and generally, a better picture of the user's health.

Figure 9A:
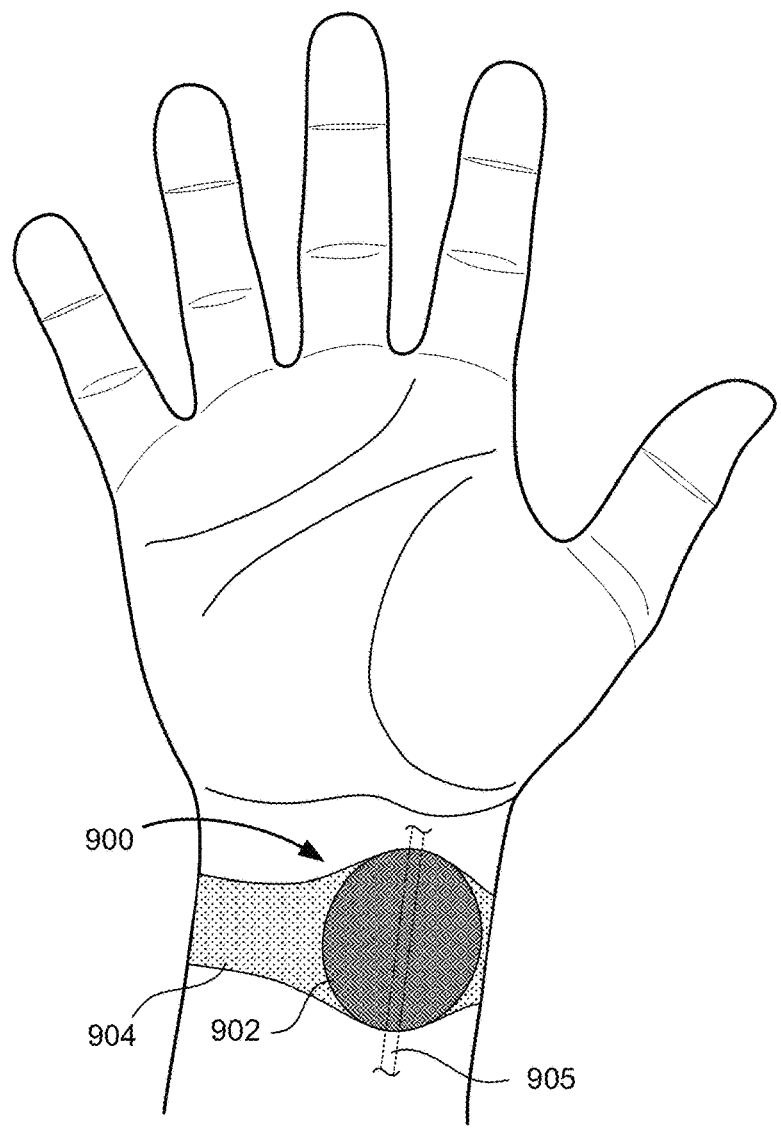
FIG. 9A shows an example ambulatory monitoring device 900 designed to be worn around a wrist according to some implementations.

In some implementations, some or all of the components of apparatus 200 of FIG. 2 may be arranged, assembled or otherwise included within a housing of an ambulatory monitoring device that can be positioned around a wrist of a user with a strap or band, similar to a watch or fitness/activity tracker. FIG. 9A shows an example ambulatory monitoring device 900 designed to be worn around a wrist according to some implementations. In the illustrated example, the monitoring device 900 includes a housing 902 integrally formed with, coupled with or otherwise integrated with a strap or band 904. In this example, the ambulatory monitoring device 900 is coupled around the wrist such that a light source system within the housing 902 will emit light pulses into tissue along a stretch of an artery 905.

Figure 9B:
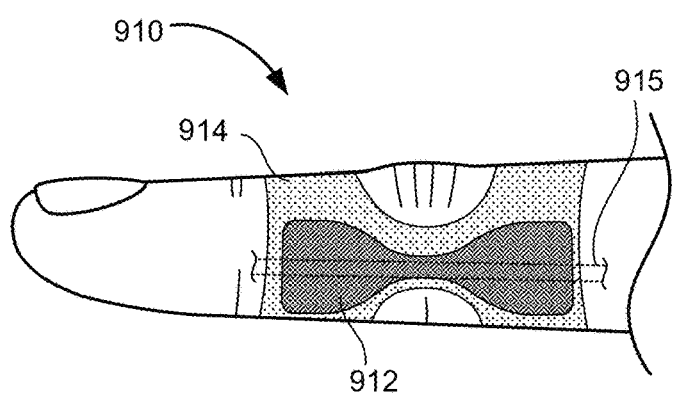
FIG. 9B shows an example ambulatory monitoring device 900 designed to be worn around a finger according to some implementations.

In some other implementations, some or all of the components of apparatus 200 of FIG. 2 may be arranged, assembled or otherwise included within a housing of an ambulatory monitoring device that can similarly be designed or adapted for positioning around a forearm, an upper arm, an ankle, a lower leg, an upper leg, or a finger, using a strap or band. FIG. 9B shows an example ambulatory monitoring device 910 designed to be worn around a finger according to some implementations. In the illustrated example, the monitoring device 910 includes a housing 912 integrally formed with, coupled with or otherwise integrated with a strap or band 914. In this example, the ambulatory monitoring device 910 is coupled around the finger such that a light source system within the housing 912 will emit light pulses into tissue along a stretch of an artery 915.

In yet other implementations, some or all of the components of apparatus 200 of FIG. 2 may be arranged, assembled or otherwise included within a housing of an ambulatory monitoring device that can be positioned on a region of interest of the user without the use of a strap or band. For example, some or all of the components of apparatus 200 of FIG. 2 may be arranged, assembled or otherwise included within a housing that is secured to the skin of a region of interest of the user using an adhesive or other suitable attachment mechanism (an example of a "patch" monitoring device).

Figure 9C:
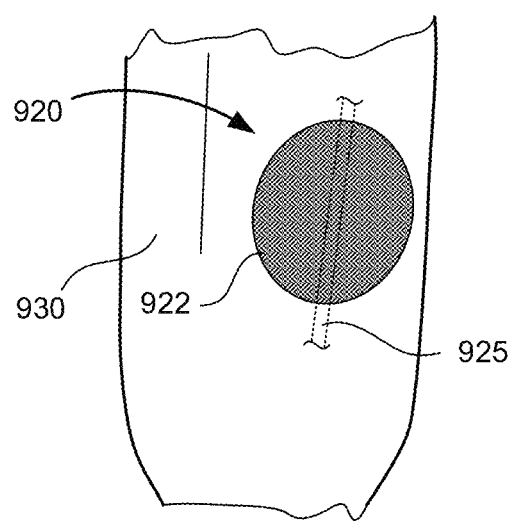
FIG. 9C shows an example ambulatory monitoring device 900 designed to reside on an earbud according to some implementations.

FIG. 9C shows an example ambulatory monitoring device 920 designed to reside on an earbud according to some implementations. According to this example, the ambulatory monitoring device 920 is coupled to the housing of an earbud 930. In this example, the ambulatory monitoring device 920 is positioned such that a light source system within the housing 922 will emit light pulses into tissue along a stretch of an artery 925.

Implementation examples are described in the following numbered clauses:

Clause 1. A biometric system, including a piezoelectric receiver, a light source system configured for emitting a plurality of light pulses, and a control system configured for controlling the light source system to emit a plurality of light pulses into biological tissue, the biological tissue including blood and blood vessels at depths within the biological tissue, receiving, from the piezoelectric receiver, signals corresponding to acoustic waves emitted from portions of the biological tissue, the acoustic waves corresponding to photoacoustic emissions from the blood and the blood vessels caused by the plurality of light pulses, generating a plethysmography image based on heart rate waveforms in the signals, and determining a blood pressure differential by comparing the plethysmography image with a reference plethysmography image.

Clause 2. The biometric system of clause 1, where the control system is configured for displaying the blood pressure differential on a display.

Clause 3. The biometric system of any of clauses 1 to 2, where the reference plethysmography image corresponds to a first heart rate cycle and the plethysmography image corresponds to a second heart rate cycle.

Clause 4. The biometric system of any of clauses 1 to 3, where the control system is configured for time-normalizing the plethysmography image and the reference plethysmography image.

Clause 5. The biometric system of any of clauses 1 to 4, where the plethysmography image includes a depth time dimension and a pulse time dimension.

Clause 6. The biometric system of any of clauses 1 to 5, where the control system is configured for identifying a ground truth blood pressure, and determining an absolute blood pressure based on the ground truth blood pressure and the blood pressure differential.

Clause 7. The biometric system of clause 6, where the control system is configured for displaying the absolute blood pressure on a display.

Clause 8. The biometric system of any of clauses 6 to 7, where the ground truth blood pressure includes a cuff-based blood pressure.

Clause 9. The biometric system of any of clauses 1 to 8, where the control system is configured for generating the reference plethysmography image based on a first raw plethysmography signal, and generating the plethysmography image based on a second raw plethysmography signal.

Clause 10. The biometric system of any of clauses 1 to 9, where the light source system is configured for emitting a plurality of light pulses at a pulse repetition frequency between 10 Hz and 1 MHz.

Clause 11. A biometric method, including controlling, via a control system, a light source system to emit a plurality of light pulses into biological tissue, the biological tissue including blood and blood vessels at depths within the biological tissue, receiving, by the control system, signals from a piezoelectric receiver, the signals corresponding to acoustic waves emitted from portions of the biological tissue, the acoustic waves corresponding to photoacoustic emissions from the blood and the blood vessels caused by the plurality of light pulses, generating, by the control system, a plethysmography image based on heart rate waveforms in the signals, and determining, by the control system, a blood pressure differential by comparing the plethysmography image with a reference plethysmography image.

Clause 12. The biometric method of clause 11, including displaying, by the control system, the blood pressure differential on a display.

Clause 13. The biometric method of any of clauses 11 to 12, where the reference plethysmography image corresponds to a first heart rate cycle and the plethysmography image corresponds to a second heart rate cycle.

Clause 14. The biometric method of any of clauses 11 to 13, including time-normalizing, by the control system, the plethysmography image and the reference plethysmography image.

Clause 15. The biometric method of any of clauses 11 to 14, where the plethysmography image includes a depth time dimension and a pulse time dimension.

Clause 16. The biometric method of any of clauses 11 to 15, including identifying, by the control system, a ground truth blood pressure, and determining, by the control system, an absolute blood pressure based on the ground truth blood pressure and the blood pressure differential.

Clause 17. The biometric method of clause 16, including displaying, by the control system, the absolute blood pressure on a display.

Clause 18. The biometric method of any of clauses 16 to 17, where the ground truth blood pressure includes a cuff-based blood pressure.

Clause 19. The biometric method of any of clauses 11 to 18, including generating, by the control system, the reference plethysmography image based on a first raw plethysmography signal, and generating, by the control system, the plethysmography image based on a second raw plethysmography signal.

Clause 20. The biometric method of any of clauses 11 to 19, where the light source system is configured for emitting a plurality of light pulses at a pulse repetition frequency between 10 Hz and 1 MHz.

Clause 21. One or more non-transitory media having software stored thereon, the software including instructions for controlling one or more devices to perform a biometric method, the biometric method including controlling, via a control system, a light source system to emit a plurality of light pulses into biological tissue, the biological tissue including blood and blood vessels at depths within the biological tissue, receiving, by the control system, signals from a piezoelectric receiver, the signals corresponding to acoustic waves emitted from portions of the biological tissue, the acoustic waves corresponding to photoacoustic emissions from the blood and the blood vessels caused by the plurality of light pulses, generating, by the control system, a plethysmography image based on heart rate waveforms in the signals, and determining, by the control system, a blood pressure differential by comparing the plethysmography image with a reference plethysmography image.

Clause 22. The one or more non-transitory media of clause 21, where the biometric method further includes displaying, by the control system, the blood pressure differential on a display.

Clause 23. The one or more non-transitory media of any of clauses 21 to 22, where the reference plethysmography image corresponds to a first heart rate cycle and the plethysmography image corresponds to a second heart rate cycle.

Clause 24. The one or more non-transitory media of any of clauses 21 to 23, where the biometric method further includes time-normalizing, by the control system, the plethysmography image and the reference plethysmography image.

Clause 25. The one or more non-transitory media of any of clauses 21 to 24, where the plethysmography image includes a depth time dimension and a pulse time dimension.

Clause 26. The one or more non-transitory media of any of clauses 21 to 25, where the biometric method further includes identifying, by the control system, a ground truth blood pressure, and determining, by the control system, an absolute blood pressure based on the ground truth blood pressure and the blood pressure differential.

Clause 27. The one or more non-transitory media of clause 26, where the biometric method further includes displaying, by the control system, the absolute blood pressure on a display.

Clause 28. The one or more non-transitory media of any of clauses 26 to 27, where the ground truth blood pressure includes a cuff-based blood pressure.

Clause 29. The one or more non-transitory media of any of clauses 21 to 28, where the biometric method further includes generating, by the control system, the reference plethysmography image based on a first raw plethysmography signal, and generating, by the control system, the plethysmography image based on a second raw plethysmography signal.

Clause 30. The one or more non-transitory media of any of clauses 21 to 29, where the light source system is configured for emitting a plurality of light pulses at a pulse repetition frequency between 10 Hz and 1 MHz.

The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single-or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

The invention claimed is:

1. A biometric system, comprising:
   a piezoelectric receiver;
   a light source system configured for emitting a plurality of light pulses; and
   a control system configured for:
      controlling the light source system to emit the plurality of light pulses into biological tissue, the biological tissue including blood and blood vessels at depths within the biological tissue;
      receiving, from the piezoelectric receiver, signals corresponding to acoustic waves emitted from portions of the biological tissue, the acoustic waves corresponding to photoacoustic emissions from the blood and the blood vessels caused by the plurality of light pulses;
      generating a plethysmography image based on heart rate waveforms in the signals, wherein the plethysmography image comprises a depth time dimension and a pulse time dimension, the depth time dimension being orthogonal to the pulse time dimension, the pulse time dimension including multiple heart rate cycles; and
      determining a blood pressure differential by comparing the plethysmography image with a reference plethysmography image.

2. The biometric system of claim 1, wherein the control system is configured for displaying the blood pressure differential on a display.

3. The biometric system of claim 1, wherein the reference plethysmography image corresponds to a first heart rate cycle and the plethysmography image corresponds to a second heart rate cycle.

4. The biometric system of claim 1, wherein the control system is configured for time-normalizing the plethysmography image and the reference plethysmography image.

5. The biometric system of claim 1, wherein the plethysmography image comprises a plurality of regions, each region of the plurality of regions corresponding to a depth time interval and a corresponding heart rate cycle.

6. The biometric system of claim 1, wherein the control system is configured for:
   identifying a ground truth blood pressure; and
   determining an absolute blood pressure based on the ground truth blood pressure and the blood pressure differential.

7. The biometric system of claim 6, wherein the control system is configured for displaying the absolute blood pressure on a display.

8. The biometric system of claim 6, wherein the ground truth blood pressure comprises a cuff-based blood pressure.

9. The biometric system of claim 1, wherein the control system is configured for:
   generating the reference plethysmography image based on a first raw plethysmography signal; and generating the plethysmography image based on a second raw plethysmography signal.

10. The biometric system of claim 1, wherein the light source system is configured for emitting the plurality of light pulses at a pulse repetition frequency between 10 Hz and 1 MHz.

11. A biometric method, comprising:
controlling, via a control system, a light source system to emit a plurality of light pulses into biological tissue, the biological tissue including blood and blood vessels at depths within the biological tissue;
receiving, by the control system, signals from a piezoelectric receiver, the signals corresponding to acoustic waves emitted from portions of the biological tissue, the acoustic waves corresponding to photoacoustic emissions from the blood and the blood vessels caused by the plurality of light pulses;
generating, by the control system, a plethysmography image based on heart rate waveforms in the signals, wherein the plethysmography image comprises a depth time dimension and a pulse time dimension, the depth time dimension being orthogonal to the pulse time dimension, the pulse time dimension including multiple heart rate cycles; and
determining, by the control system, a blood pressure differential by comparing at least a portion of the plethysmography image with at least a portion of a reference plethysmography image.

12. The biometric method of claim 11, comprising displaying, by the control system, the blood pressure differential on a display.

13. The biometric method of claim 11, wherein the reference plethysmography image corresponds to a first heart rate cycle and the plethysmography image corresponds to a second heart rate cycle.

14. The biometric method of claim 11, comprising time-normalizing, by the control system, the plethysmography image and the reference plethysmography image.

15. The biometric method of claim 11, wherein the plethysmography image comprises a plurality of regions, each region of the plurality of regions corresponding to a depth time interval and a corresponding heart rate cycle.

16. The biometric method of claim 11, comprising:
identifying, by the control system, a ground truth blood pressure; and
determining, by the control system, an absolute blood pressure based on the ground truth blood pressure and the blood pressure differential.

17. The biometric method of claim 16, comprising displaying, by the control system, the absolute blood pressure on a display.

18. The biometric method of claim 16, wherein the ground truth blood pressure comprises a cuff-based blood pressure.

19. The biometric method of claim 11, comprising:
generating, by the control system, the reference plethysmography image based on a first raw plethysmography signal; and
generating, by the control system, the plethysmography image based on a second raw plethysmography signal.

20. The biometric method of claim 11, wherein the light source system is configured for emitting the plurality of light pulses at a pulse repetition frequency between 10 Hz and 1 MHz.

21. One or more non-transitory media having software stored thereon, the software including instructions for performing a biometric method, the biometric method comprising:

controlling, via a control system, a light source system to emit a plurality of light pulses into biological tissue, the biological tissue including blood and blood vessels at depths within the biological tissue;
receiving, by the control system, signals from a piezoelectric receiver, the signals corresponding to acoustic waves emitted from portions of the biological tissue, the acoustic waves corresponding to photoacoustic emissions from the blood and the blood vessels caused by the plurality of light pulses;
generating, by the control system, a plethysmography image based on heart rate waveforms in the signals, wherein the plethysmography image comprises a depth time dimension and a pulse time dimension, the depth time dimension being orthogonal to the pulse time dimension, the pulse time dimension including multiple heart rate cycles; and
determining, by the control system, a blood pressure differential by comparing at least a portion of the plethysmography image with at least a portion of a reference plethysmography image.

22. The one or more non-transitory media of claim 21, wherein the biometric method further comprises displaying, by the control system, the blood pressure differential on a display.

23. The one or more non-transitory media of claim 21, wherein the reference plethysmography image corresponds to a first heart rate cycle and the plethysmography image corresponds to a second heart rate cycle.

24. The one or more non-transitory media of claim 21, wherein the biometric method further comprises time-normalizing, by the control system, the plethysmography image and the reference plethysmography image.

25. The one or more non-transitory media of claim 21, wherein the plethysmography image comprises a plurality of regions, each region of the plurality of regions corresponding to a depth time interval and a corresponding heart rate cycle.

26. The one or more non-transitory media of claim 21, wherein the biometric method further comprises:
identifying, by the control system, a ground truth blood pressure; and
determining, by the control system, an absolute blood pressure based on the ground truth blood pressure and the blood pressure differential.

27. The one or more non-transitory media of claim 26, wherein the biometric method further comprises displaying, by the control system, the absolute blood pressure on a display.

28. The one or more non-transitory media of claim 26, wherein the ground truth blood pressure comprises a cuff-based blood pressure.

29. The one or more non-transitory media of claim 21, wherein the biometric method further comprises:
generating, by the control system, the reference plethysmography image based on a first raw plethysmography signal; and
generating, by the control system, the plethysmography image based on a second raw plethysmography signal.

30. The one or more non-transitory media of claim 21, wherein the light source system is configured for emitting the plurality of light pulses at a pulse repetition frequency between 10 Hz and 1 MHz.

* * * * *